US011224515B2

(12) United States Patent
Bordeaux et al.

(10) Patent No.: US 11,224,515 B2
(45) Date of Patent: Jan. 18, 2022

(54) IMPLANTS/PROCEDURES RELATED TO TIBIAL TUBEROSITY ADVANCEMENT

(71) Applicant: DePuy Synthes Products, Inc., Raynham, MA (US)

(72) Inventors: Jean-Noel Bordeaux, West Chester, PA (US); Timothy J. Horan, Royersford, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 56 days.

(21) Appl. No.: 15/013,172

(22) Filed: Feb. 2, 2016

(65) Prior Publication Data

US 2016/0151160 A1 Jun. 2, 2016

Related U.S. Application Data

(62) Division of application No. 13/785,028, filed on Mar. 5, 2013, now abandoned.
(Continued)

(51) Int. Cl.
*A61F 2/38* (2006.01)
*A61F 2/30* (2006.01)
(Continued)

(52) U.S. Cl.
CPC ........ *A61F 2/30724* (2013.01); *A61B 17/025* (2013.01); *A61B 17/1764* (2013.01); *A61B 17/8061* (2013.01); *A61B 17/8095* (2013.01); *A61B 17/8866* (2013.01); *A61F 2/30734* (2013.01); *A61F 2/389* (2013.01); *A61B 17/1675* (2013.01); *A61B 17/8057* (2013.01); *A61B 17/848* (2013.01); *A61B 17/8863* (2013.01); *A61B 2017/0268* (2013.01); *A61B 2017/564* (2013.01); *A61B 2090/061* (2016.02); *A61B 2090/067* (2016.02)

(58) Field of Classification Search
CPC .. A61F 2/30724; A61F 2/389; A61B 17/1764; A61B 17/8095; A61B 2017/564
See application file for complete search history.

(56) References Cited

U.S. PATENT DOCUMENTS 6,077,266 A * 6/2000 Medoff ................. A61B 17/80
128/898
2002/0165552 A1 11/2002 Duffner
(Continued)

FOREIGN PATENT DOCUMENTS

| CN | 1997329 | 7/2007 |
|---|---|---|
| WO | WO 2013/187950 | 12/2003 |
| WO | WO 2012/075349 | 6/2012 |

OTHER PUBLICATIONS

Lafaver et al., "Tibial Tuberosity Advancement for Stabilization of the Canine Cranial Cruciate Ligament-Deficient Stifle Joint: Surgical Technique, Early Results and Complications in 101 Dogs", Veterinary Surgery, Aug. 2007, 36, p. 573-586.*
(Continued)

*Primary Examiner* — Christopher D. Prone
(74) *Attorney, Agent, or Firm* — BakerHostetler

(57) ABSTRACT

A tibial tuberosity advancement (TTA) system is configured to maintaining a tuberosity in an advanced position relative to a tibial body. The TTA system includes an implant, a spacer, and a spacer fixation member.

8 Claims, 19 Drawing Sheets

Related U.S. Application Data

(60) Provisional application No. 61/659,655, filed on Jun. 14, 2012.

(51) Int. Cl.

| | | |
|---|---|---|
| *A61B 17/80* | (2006.01) | |
| *A61B 17/88* | (2006.01) | |
| *A61B 17/17* | (2006.01) | |
| *A61B 17/02* | (2006.01) | |
| *A61B 17/56* | (2006.01) | |
| *A61B 17/84* | (2006.01) | |
| *A61B 17/16* | (2006.01) | |
| *A61B 90/00* | (2016.01) | |

(56) References Cited

U.S. PATENT DOCUMENTS

| | | |
|---|---|---|
| 2005/0075641 A1 | 4/2005 | Singhatat et al. |
| 2006/0025776 A1 | 2/2006 | Thorsgard |
| 2006/0212035 A1 | 9/2006 | Wotton |
| 2007/0213830 A1 | 9/2007 | Ammann et al. |
| 2008/0195099 A1 | 8/2008 | Minas |
| 2008/0269808 A1* | 10/2008 | Gall ............... A61B 17/7225 606/299 |
| 2009/0326590 A1 | 12/2009 | Foley et al. |
| 2010/0076564 A1 | 3/2010 | Schilling et al. |
| 2011/0172774 A1 | 7/2011 | Varela |
| 2012/0197410 A1 | 8/2012 | Horan et al. |

OTHER PUBLICATIONS

U.S. Appl. No. 61/659,655, filed Jun. 14, 2012, Bordeaux et al.

International Patent Application No. PCT/US2013/028976: International Search Report dated Sep. 21, 2013, 21 pages.

Lafaver et al., "Tibial Tuberosity Advancement for Stablization of the Canine Cranial Cruciate Ligament-Deficient Stifle Joint: Surgical Technique, Early Results and Complications in 101 Dogs", Veterinary Surgery, Aug. 2007, 36, 573-586.

* cited by examiner

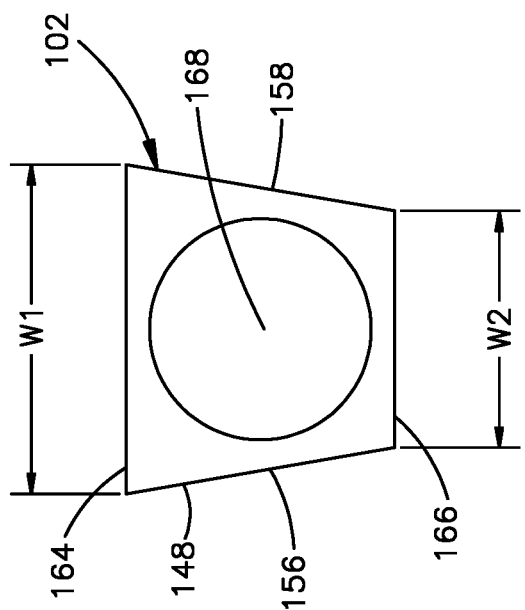
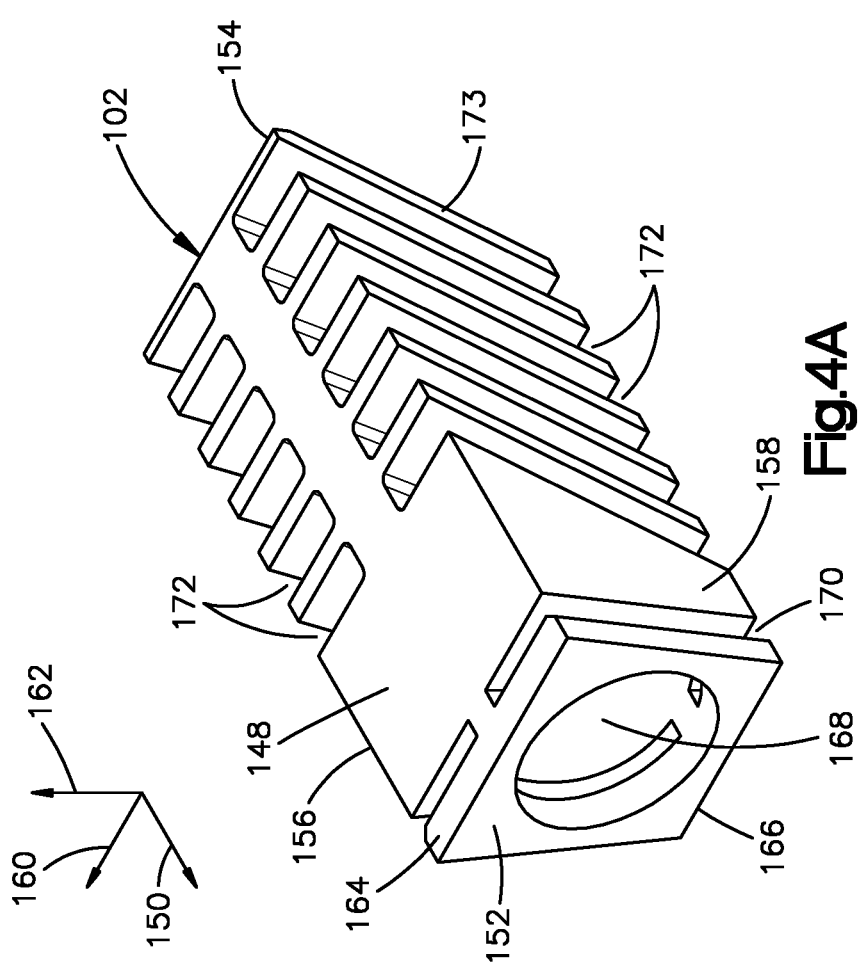

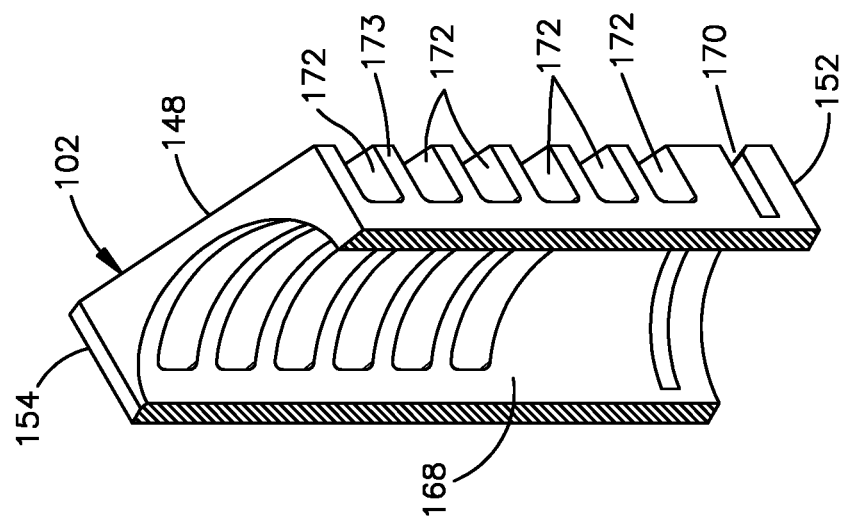
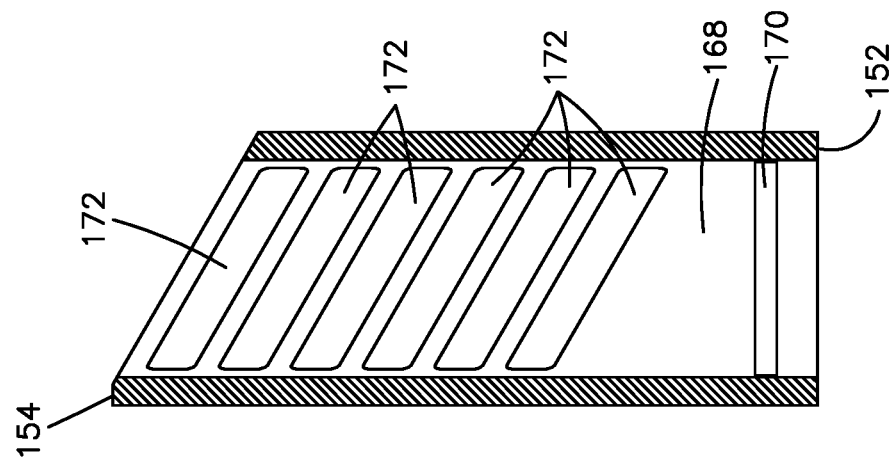
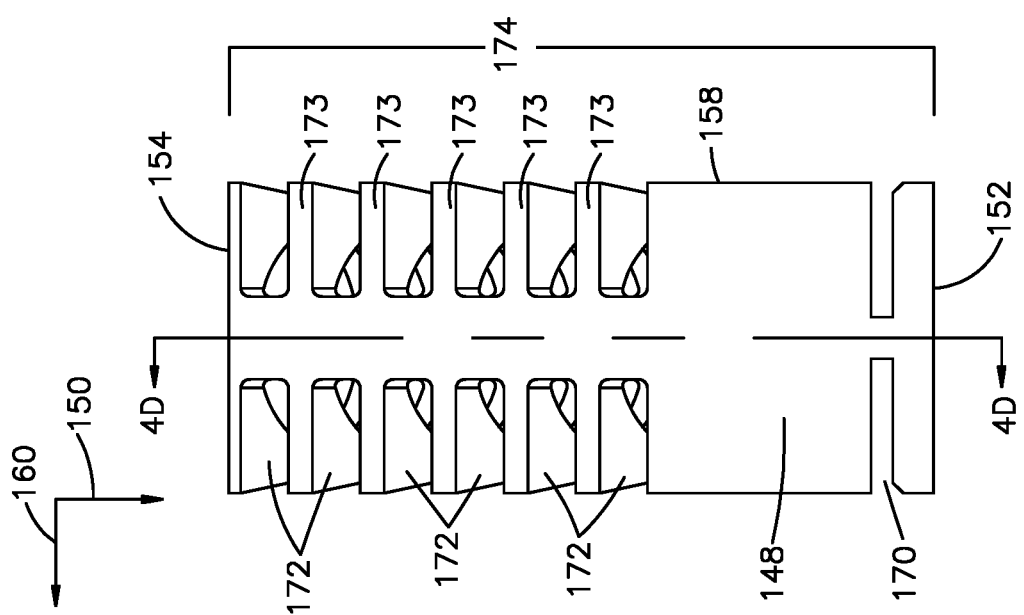
Fig.4E
Fig.4D
Fig.4C

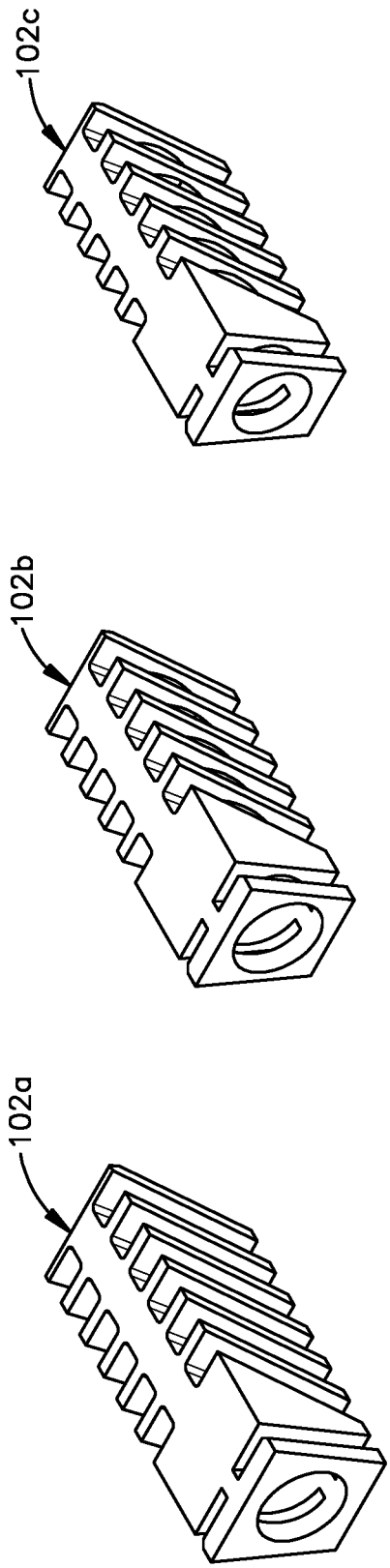
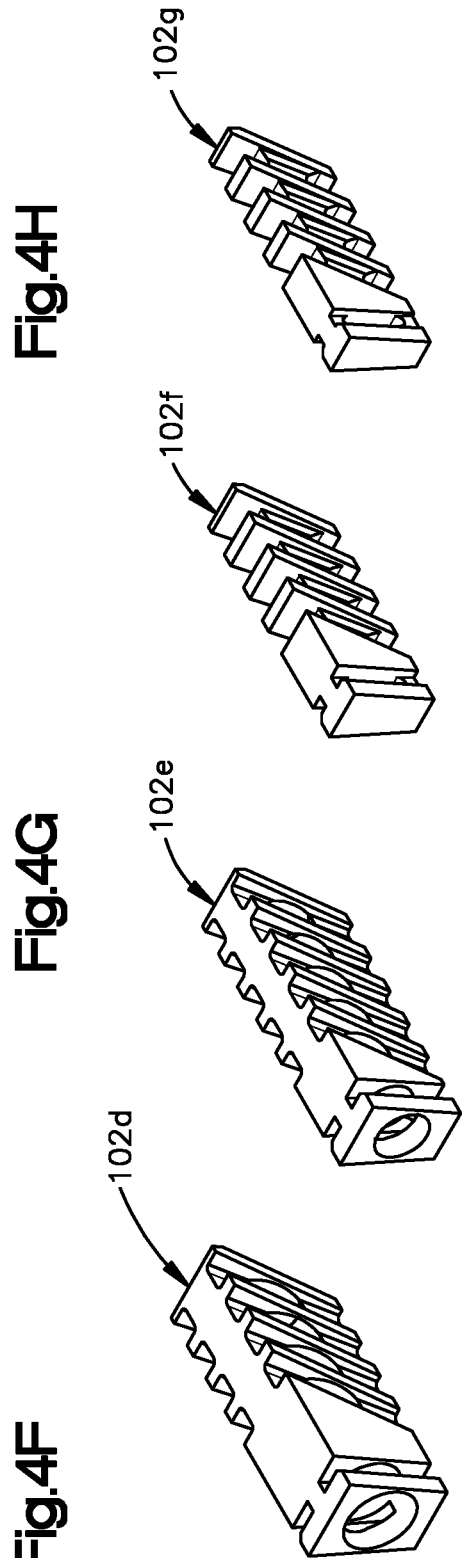
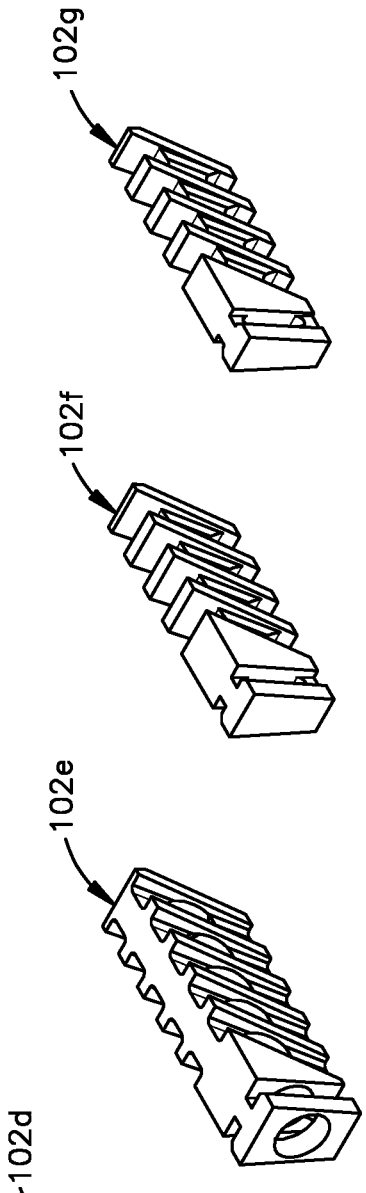
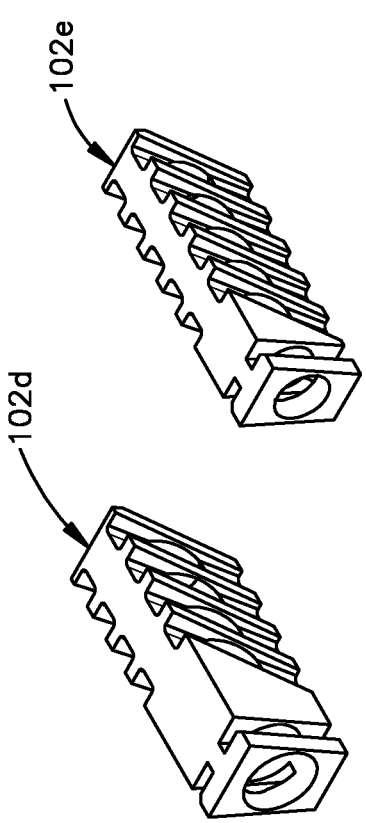
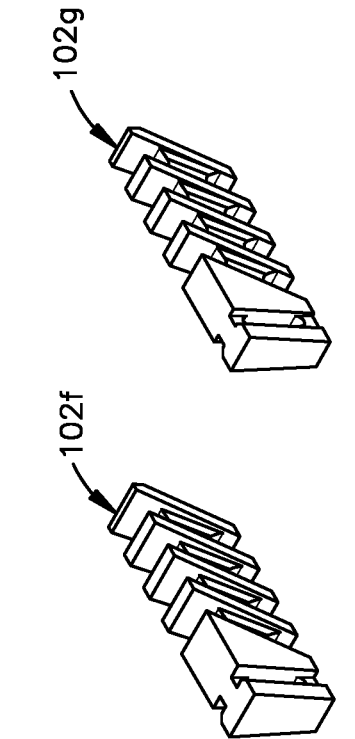

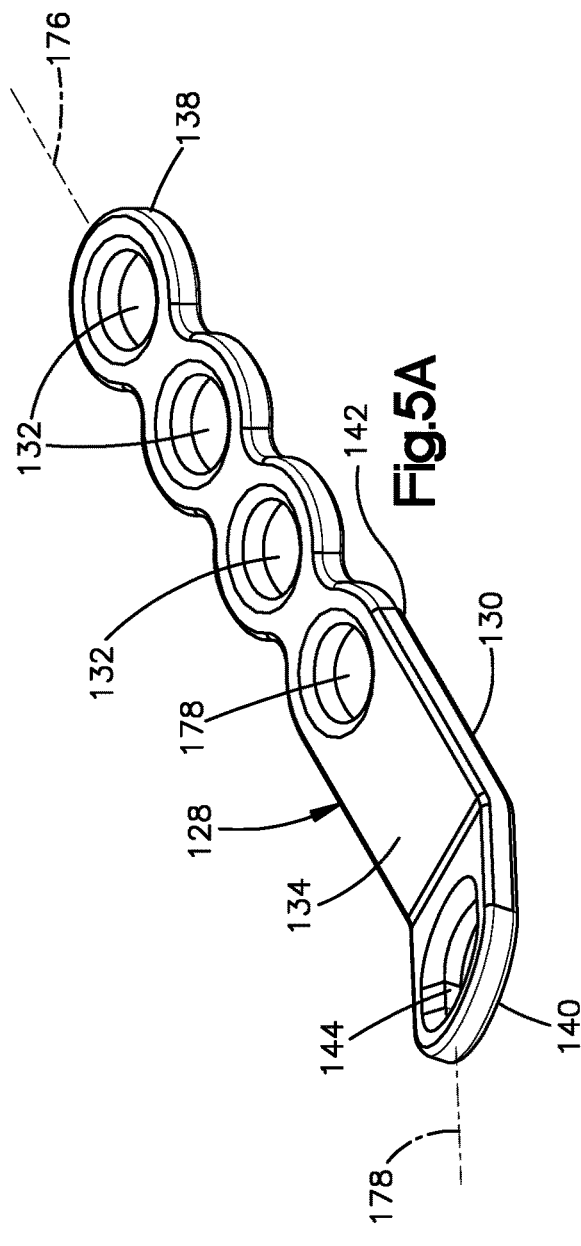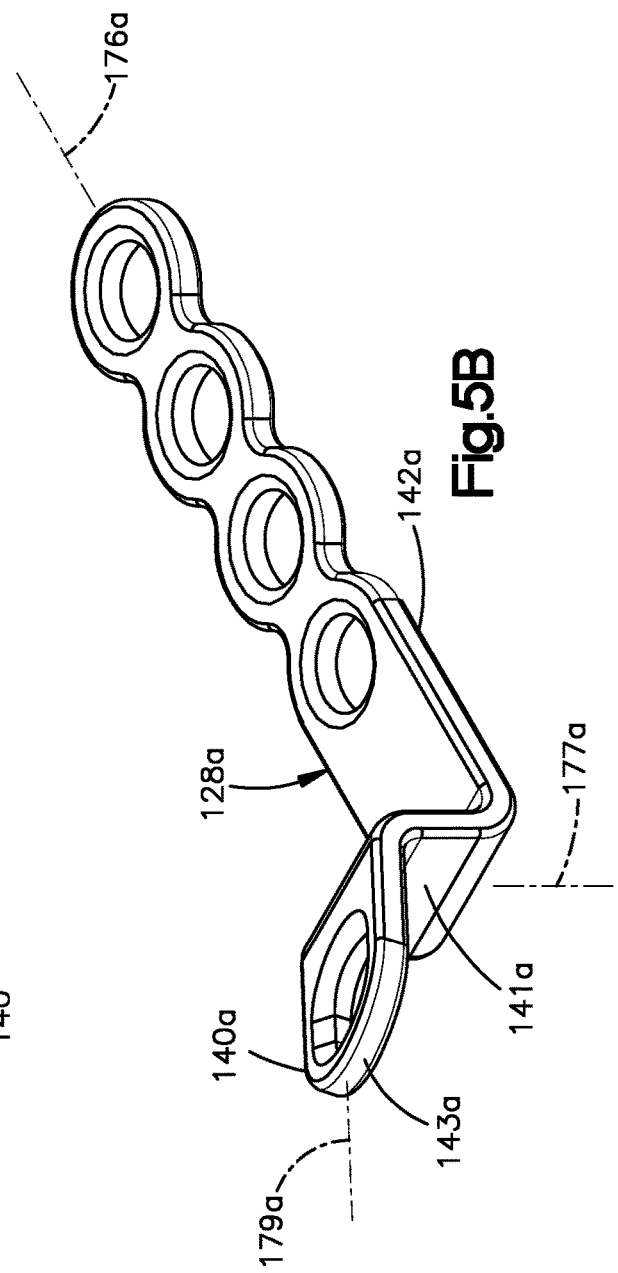

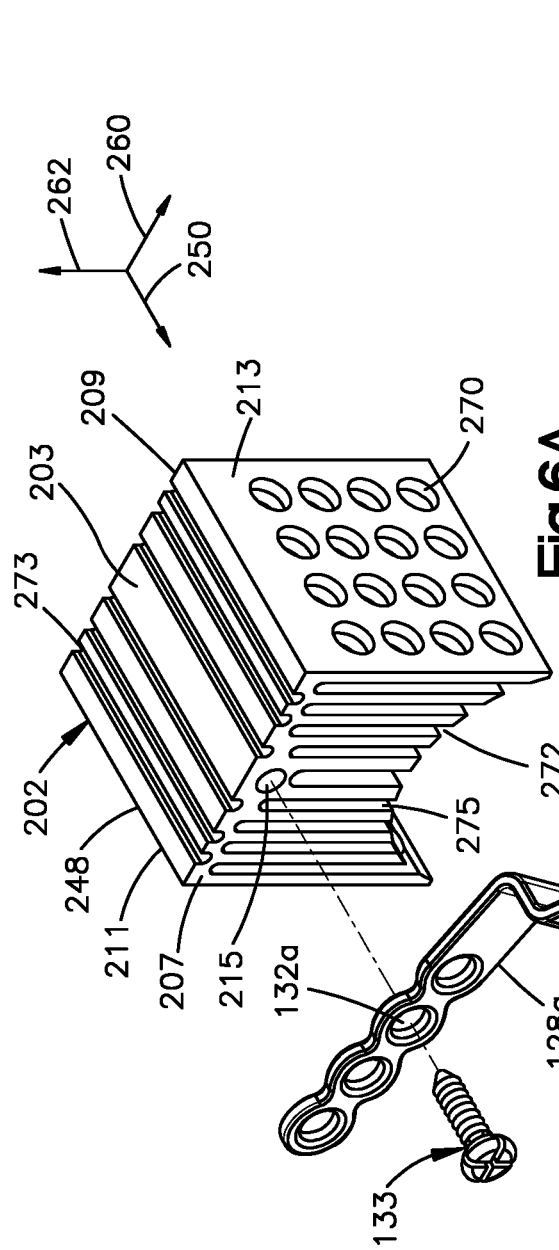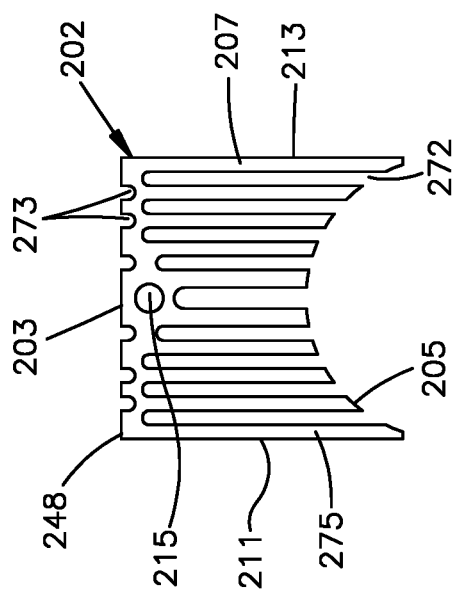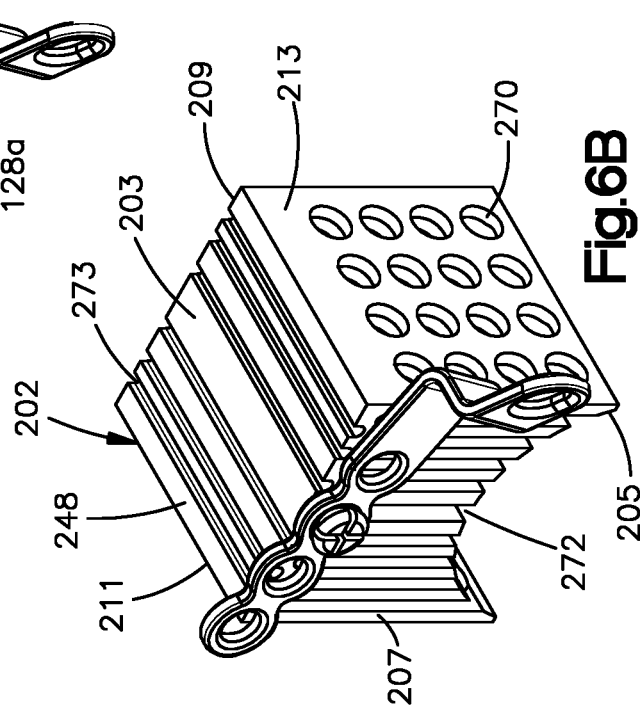

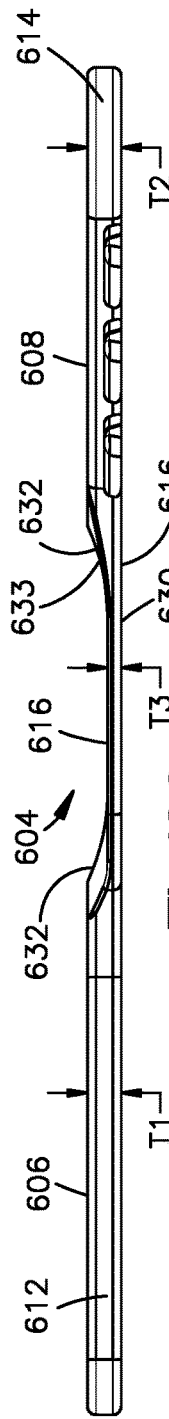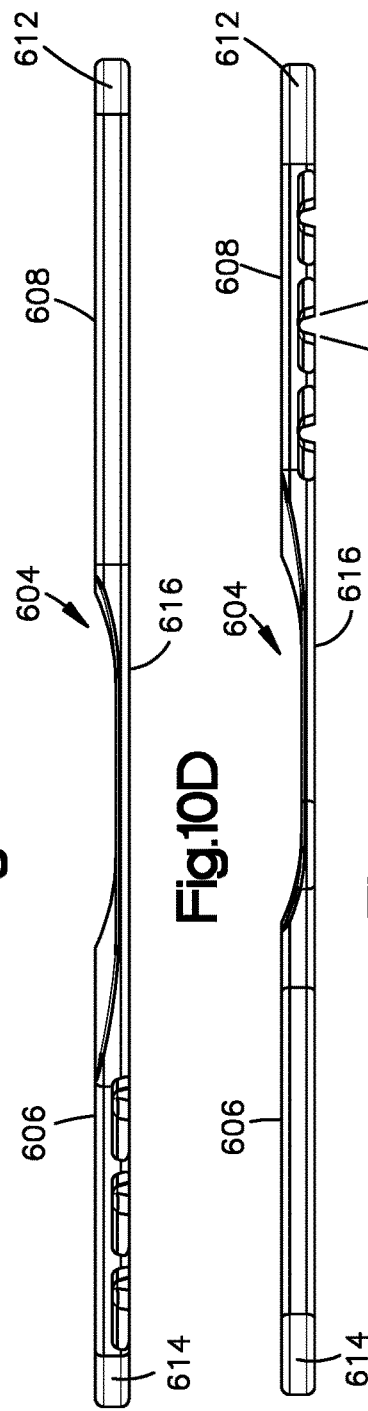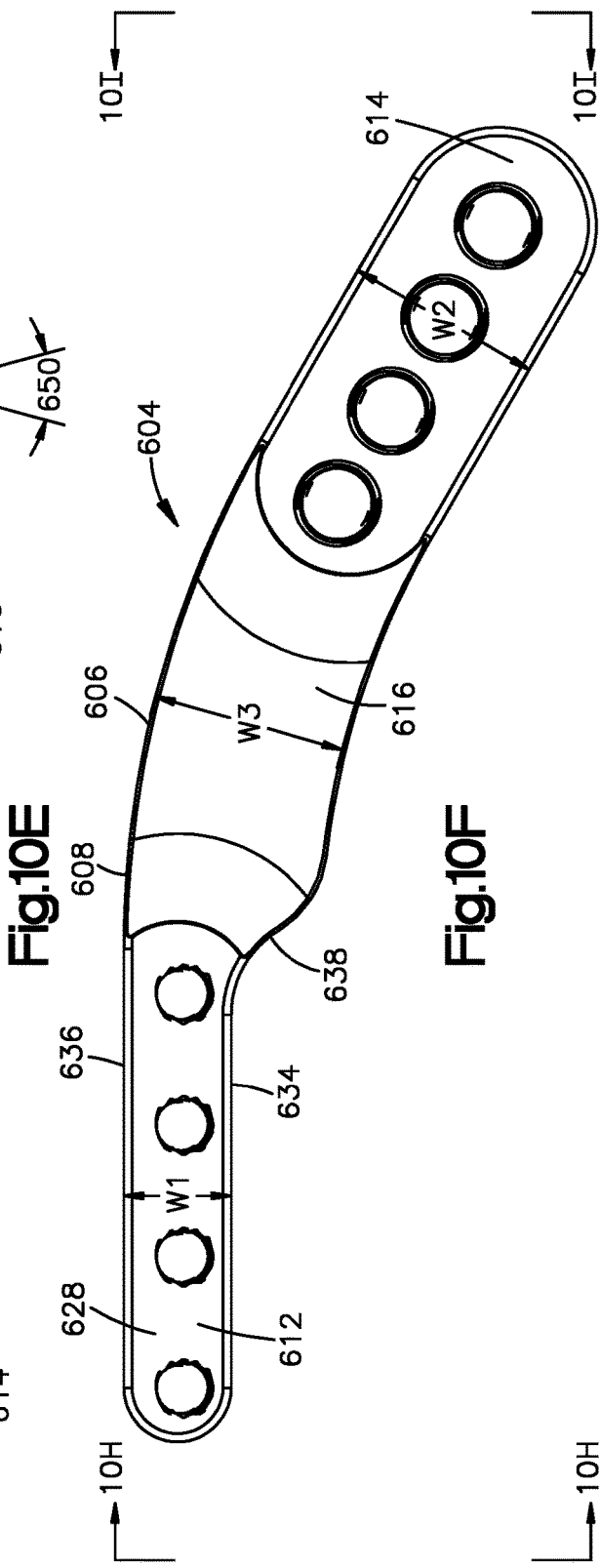

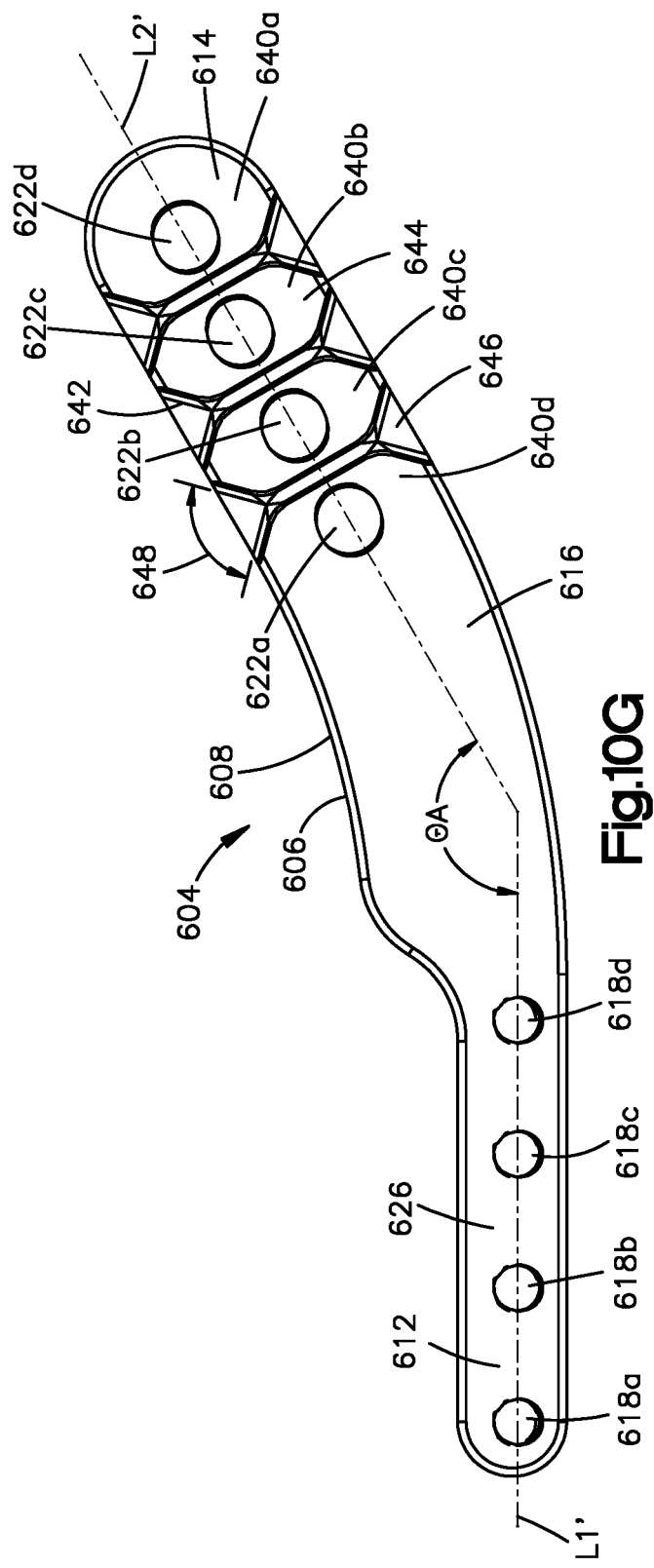

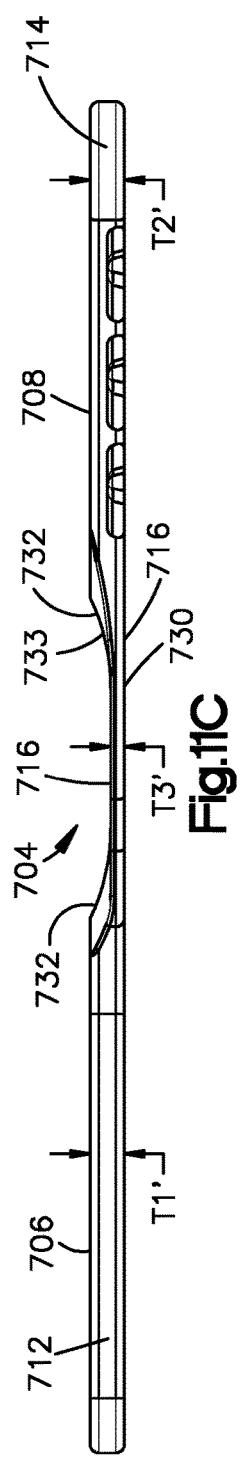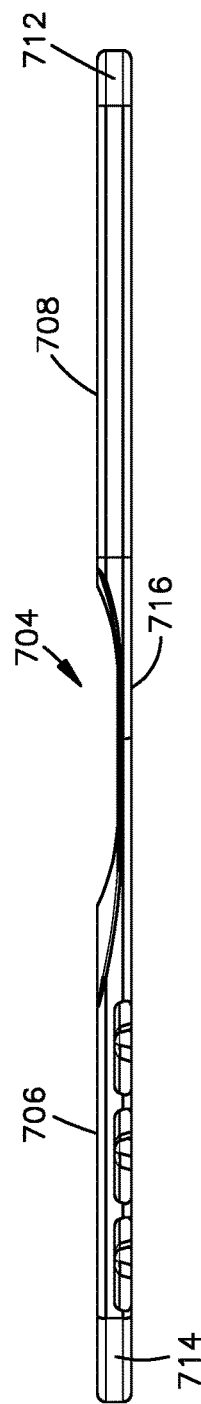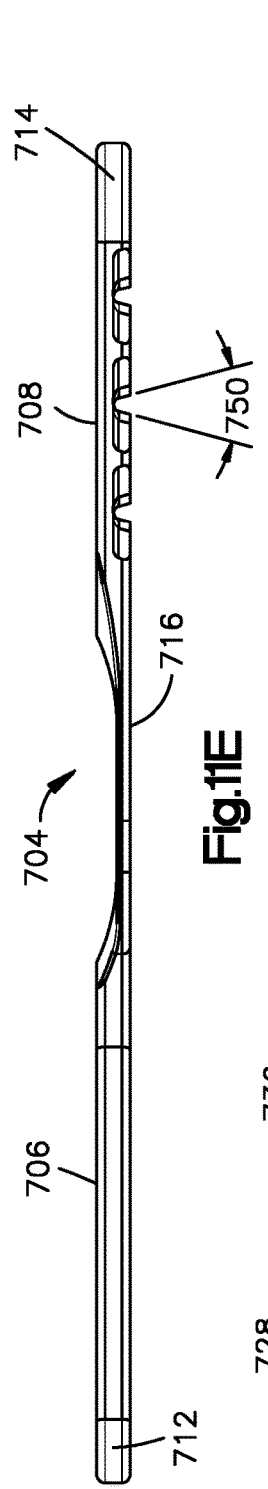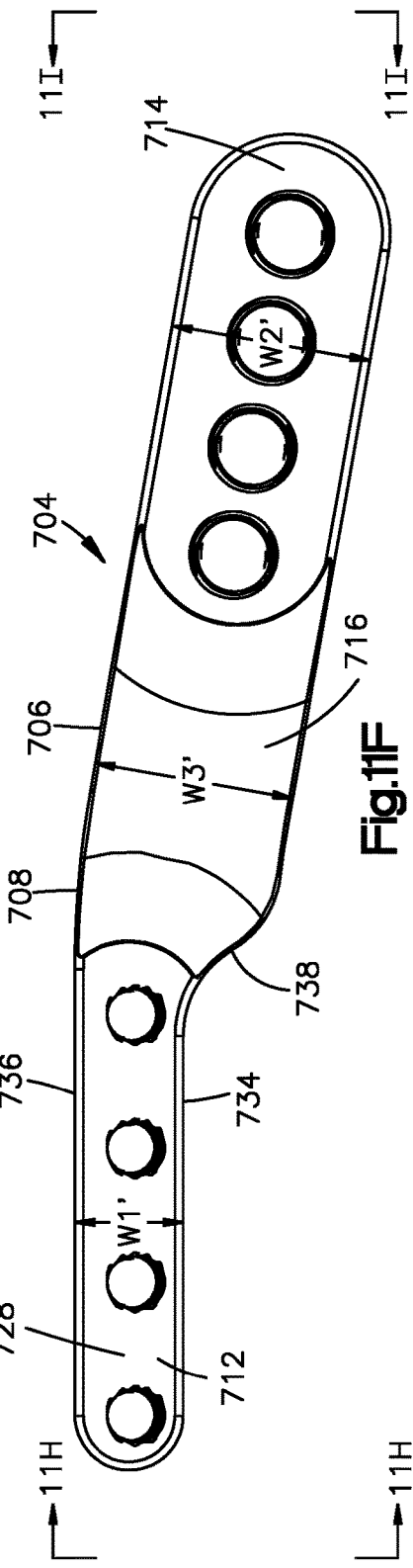

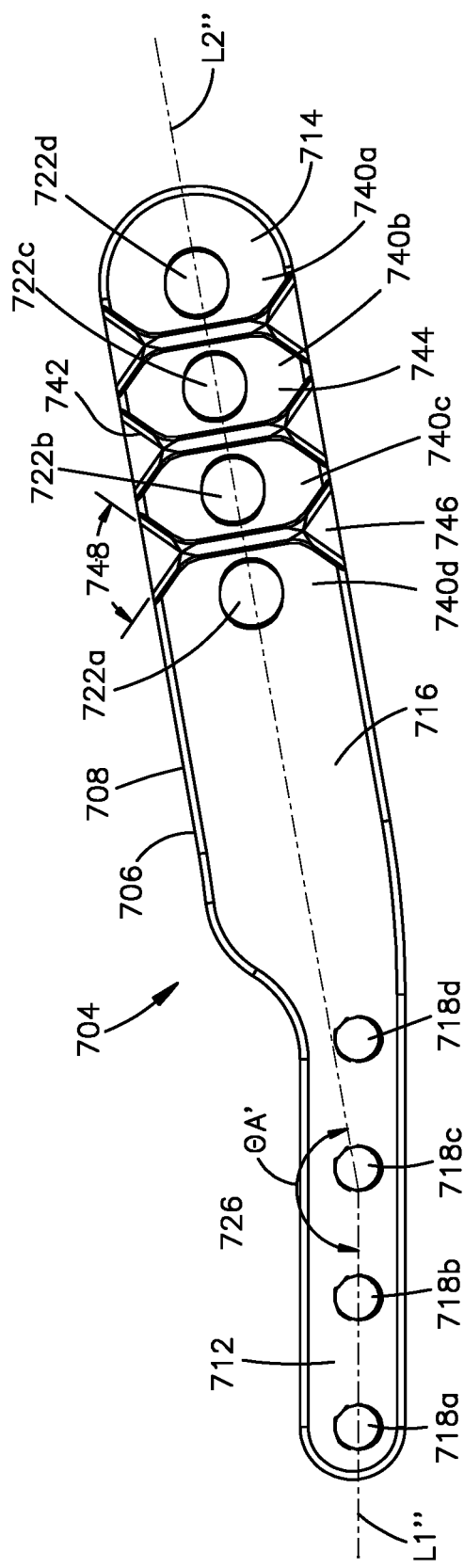

IMPLANTS/PROCEDURES RELATED TO TIBIAL TUBEROSITY ADVANCEMENT

CROSS REFERENCE TO RELATED APPLICATIONS

This application is a divisional of U.S. patent application Ser. No. 13/785,028, filed Mar. 5, 2013, which claims benefit to U.S. Provisional Application No. 61/659,655, filed Jun. 14, 2012, the disclosures of which are hereby incorporated by reference herein in their entireties.

TECHNICAL FIELD

The present application generally relates to systems, apparatus, and methods for stabilizing a deficient stifle, and more particularly, to systems, apparatus, and methods for performing a tibial tuberosity advancement procedure.

BACKGROUND

Referring to FIG. 1, the knee joint 20 of quadrupeds, such as dogs and cats, connects the tibia 22 and the femur 24 in a pivotal relationship. The knee joint 20 includes a number of stabilizing tendons and ligaments that supports the joint during anatomical function. For instance, the cranial cruciate ligament (CCL), similar to the anterior cruciate ligament in humans, bears the majority of the animal's weight, and is important to the overall stability of the knee joint 20. The CCL is attached to the tibia 22 and the femur 24, and in general prevents or limits sliding of the tibia 22 forward or cranially relative to the femur 24, and further limits internal rotation of the tibia 22 relative to the femur 24 as well as hyperextension of the knee joint 20. The knee joint 20 further includes a meniscus 26 that is disposed between the tibia 22 and the femur 24, and absorbs impact and provides a gliding surface between the femur 24 and tibial plateau 28 of the tibia 22.

The tibia 22 includes a tibial body 23 and a tuberosity 30 that extends from the tibial body 23. The patellar tendon 32 is anchored between the tuberosity 30 and the femur 24. As illustrated in FIG. 1, a line 27 extending through the patellar tendon 32 that is both normal to the patellar tendon and directed toward the tibial plateau 28 is angularly offset with respect to a line 29 that lies in the plane generally defined by the tibial plateau 28, and intersects the line 27 at a location between the patellar tendon 32 and the tibial plateau 28. Accordingly, when the CCL is damaged, which is a common injury in canines, the patellar ligament 32 does not prevent the femur 24 from travelling along the tibial plateau 28 due to tibiofemoral sheer forces when weight is applied to the injured knee join 20. As a result, damage to the CCL often results in lameness of the affected knee, damage to the meniscus 26 due to forces applied by the femur 24, and degenerative joint diseases. Furthermore, the animal can tend to overcompensate for the injured knee joint 20, which can result in rupture of the CCL of the other knee during a weight-bearing anatomical function.

Referring also to FIG. 2, tibial tuberosity advancement (TTA) is a procedure designed to repair a knee joint 20 that has been affected by a damaged cranial cruciate ligament. Conventional TTAs include the step of performing an osteotomy cut to separate the tibial tuberosity 30 from the tibial body 23, and subsequently advancing the tibial tuberosity 30, and thus also the patellar tendon 32, cranially to a position spaced from the tibia 22 so as to define a gap 40 between the tibial tuberosity 30 and the tibial body 23. For instance, during a TTA, the tibial tuberosity 30 and the patellar tendon 32 are typically advanced such that the line 27 extending through the patellar tendon 32 that is both normal to the patellar tendon 32 and directed toward the tibial plateau 28 is also substantially parallel to, and can be coincident with, the line 29 that lies in the plane generally defined by the tibial plateau 28. Thus, the line 27 can be substantially parallel to or coincident with the plane defined by the tibial plateau 28. In general, the line 27 is more parallel to, or coincident with, the line 29, and thus the plane defined by the tibial plateau 28, after the TTA than before the TTA. The tibial tuberosity 30 is then fixed in the advanced position, which neutralizes the tibiofemoral sheer force when weight is applied to the knee joint 20, thereby reducing or altogether bypassing the anatomical function of the CCL.

Thus, with continuing reference to FIG. 2, a conventional TTA system 34 includes a bone plate 36 that is connected to the tibia 22 at one end, and to the advanced tibial tuberosity 30 at another end so as to provide fixation of the advanced tibial tuberosity 30 and the tibial body 23, and a spacer 38 in the form of a cage that is separate from the bone plate 36 and is disposed and connected between the advanced tibial tuberosity 30 and the tibial body 23 so as to maintain the gap 40 between the tibial tuberosity 30 and the tibial body 23 against the caudally-directed force of the patellar tendon 32.

A number instruments, apparatus, systems, and methods have been developed to conduct TTA procedures in dogs. However, improvements to those instruments and implants are still desired.

SUMMARY

The present disclosure relates to TTA systems for maintaining an advanced tuberosity in an advanced position relative to a tibial body. The advanced position of the tuberosity is spaced cranially and proximally with respect to a first position when the tuberosity is integral with the tibial body. In one embodiment, the TTA system generally includes an implant, a spacer, and a spacer fixation member. The implant includes an implant body that defines a proximal end portion that configured to support the advanced tuberosity in the advanced position, a distal end portion that is configured to be attached to the tibial body, and an intermediate implant portion that extends between the proximal end portion and distal end portion. The intermediate portion is shaped so as to space the proximal end cranially and proximally with respect to the distal end portion an amount, or a distance, sufficient so as to maintain the advanced tuberosity in the advanced position. The spacer is configured and sized to fit within a gap disposed between the advanced tuberosity and the tibial body 23 when the distal end portion and the proximal end portion are attached to the tibial body 23 and the advanced tuberosity, respectively. The spacer includes a spacer body, and defines a slot that extends through the spacer body. The spacer fixation member includes a first end portion configured to be attached to the advanced tuberosity, a second end portion that is configured to be attached to the tibial body, and an intermediate fixation portion extending between the first end and the second end. The intermediate fixation portion is configured and sized to be at least partially received in the slot so as to couple the spacer fixation member to the spacer.

The present disclosure further relates to TTA advancement assemblies that are configured to advance a tuberosity from a first position to an advanced position relative to a tibial body after an osteotomy has been made between the tuberosity and the tibial body. In an embodiment, the TTA advancement assembly includes an advancement body that is configured to be coupled to the tibial body, and a distraction arm movably coupled to the advancement body. The distraction arm is configured to be coupled to the tuberosity, and is configured to translate to move along with the tuberosity relative to the tibial body, such that the distraction arm moves a predetermined distance relative to the advancement body. The translation of the distraction arm over the predetermined distance causes the advancement assembly to provide an indication that the tuberosity has advanced from the first position to the advanced position.

In an embodiment, the TTA advancement assembly includes an advancement body that is configured to be coupled to the tibial body; and an angular adjustment member pivotally coupled to the advancement body. The angular adjustment member is configured to pivot relative to the advancement body about a pivot axis, and includes a contact member that is configured to fit in a gap defined by the osteotomy. The angular adjustment member is configured to be pivotally fixed relative to the advancement body such that the advancement body is oriented at a predetermined advancement angle relative to the osteotomy when the contact member is disposed in the osteotomy.

The present disclosure further relates to TTA methods for advancing a tuberosity from a first position to an advanced position relative to a tibial body after an osteotomy has been made between the tuberosity and the tibial body. In an embodiment, the TTA method includes one or more of the following steps: a) coupling an advancement body to the tuberosity via a distraction arm that is movably coupled to the advancement body, the distraction arm configured to translate relative to the advancement body; b) placing a contact member that is coupled to the advancement body in a gap formed during the osteotomy, the gap disposed between the tuberosity and the tibial body; c) moving the distraction arm relative to the advancement body to move the tuberosity between the first position and the advanced position.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 4A is a perspective view of a spacer in accordance with an embodiment of the present disclosure;

FIG. 4B is a front elevation view of the spacer shown in FIG. 4A;

FIG. 4C is a top view of the spacer shown in FIG. 4A;

FIG. 4D is a side cross-sectional view of the spacer shown in FIG. 4A, taken along section line 4D-4D;

FIG. 4E is a sectional view of the spacer in FIG. 4A, taken along section line 4D-4D;

FIG. 4F is a perspective view of a spacer in accordance with one embodiment;

FIG. 4G is a perspective view of a spacer in accordance with another embodiment;

FIG. 4H is a perspective view of a spacer in accordance with another embodiment;

FIG. 4I is a perspective view of a spacer in accordance with another embodiment;

FIG. 4J is a perspective view of a spacer in accordance with another embodiment;

FIG. 4K is a perspective view of a spacer in accordance with another embodiment;

FIG. 4L is a perspective view of a spacer in accordance with another embodiment;

FIG. 5A is a perspective view of the spacer fixation member shown in FIG. 3;

FIG. 5B is a perspective view of a spacer fixation member in accordance with another embodiment;

FIG. 6A is a perspective exploded view of a spacer in accordance with another embodiment, the spacer fixation member shown in FIG. 5B, and a fastener;

FIG. 6B is a perspective view of the spacer, the spacer fixation member, and the fastener shown in FIG. 6A connected to each other;

FIG. 6C is a front elevation view of the spacer shown in FIG. 6A;

FIG. 10C is a left side elevation view of the implant shown in FIG. 10A in a first orientation;

FIG. 10D is a right side elevation view of the implant shown in FIG. 10A;

FIG. 10E is a left side elevation view of the implant shown in FIG. 10A in a second orientation;

FIG. 10F is a top plan view of the implant shown in FIG. 10A;

FIG. 10G is a bottom plan view of the implant shown in FIG. 10A;

FIG. 10H is a front elevation view of the implant shown in FIG. 10F, in the direction of line 10H;

FIG. 10I is a rear elevation view of the implant shown in FIG. 10F, in the direction of line 10I;

FIG. 11C is a left side elevation view of the implant shown in FIG. 11A in a first orientation;

FIG. 11D is a right side elevation view of the implant shown in FIG. 11A;

FIG. 11E is a left side elevation view of the implant shown in FIG. 11A in a second orientation;

FIG. 11F is a top plan view of the implant shown in FIG. 11A;

FIG. 11G is a bottom plan view of the implant shown in FIG. 11A;

FIG. 11H is a front elevation view of the implant shown in FIG. 11F, in the direction of line 11H;

FIG. 11I is a rear elevation view of the implant shown in FIG. 11F, in the direction of line 11I.

DETAILED DESCRIPTION OF THE DRAWINGS

Figure 8A:
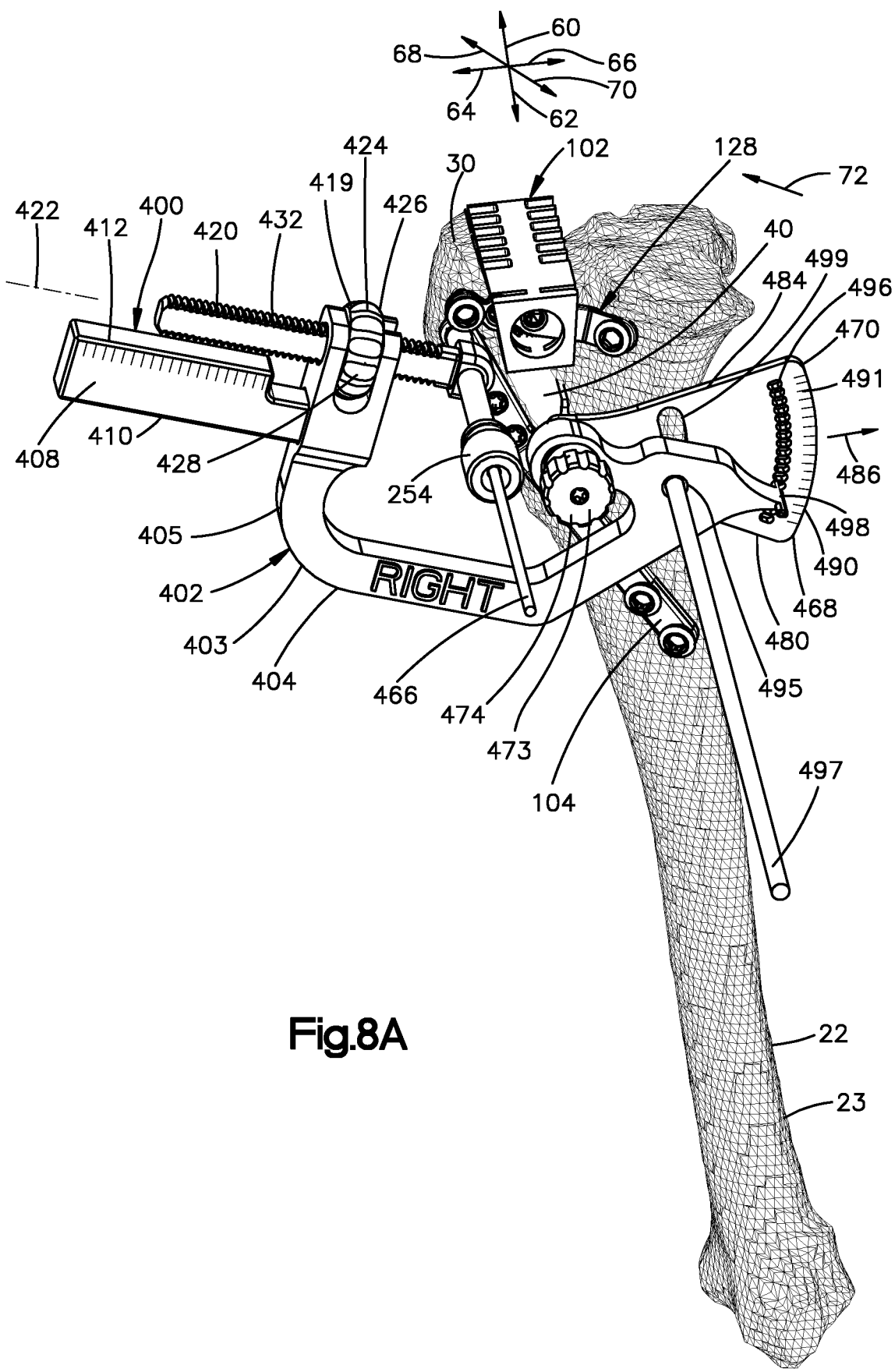
FIG. 8A is a perspective view of a guide assembly configured to guide the advancement of a tuberosity relative to a tibial body, the spacer shown in FIG. 3, the spacer fixation member shown in FIG. 3, and the implant shown in FIG. 3, wherein the guide assembly is coupled to the advanced tuberosity and the tibial body.

Certain terminology is used in the following description for convenience only and is not limiting. The words "right", "left", "lower" and "upper" designate directions in the drawings to which reference is made. The words "medially" and "laterally" refer to directions toward and away from, respectively, a midline extending through a body, for example from a head to a tail of a canine body. The words "proximal" and "distal" refer to directions toward or away from where an appendage is joined to the rest of the body. The words "anterior", "posterior", "dorsal", "ventral" and related words and/or phrases designate preferred positions and orientations in the canine body to which reference is made and are not meant to be limiting. For example "anterior" and "posterior" refer to positions closer to the head and tail, respectively. While "dorsal" and "ventral" refer to positions closer to the spinal column and the belly, respectively. The terminology includes the above-listed words, derivatives thereof and words of similar import. For example, as shown in FIG. 8A, the arrow 60 may represent the proximal, dorsal, or upward direction. The arrow 62 may represent the distal, ventral, or downward direction. The arrow 64 may represent the front, cranial or anterior direction. The arrow 66 may represent the caudal, rear or posterior direction. The arrow 68 may represent the lateral or away direction. The arrow 70 may represent the medial or toward direction.

Figure 3:
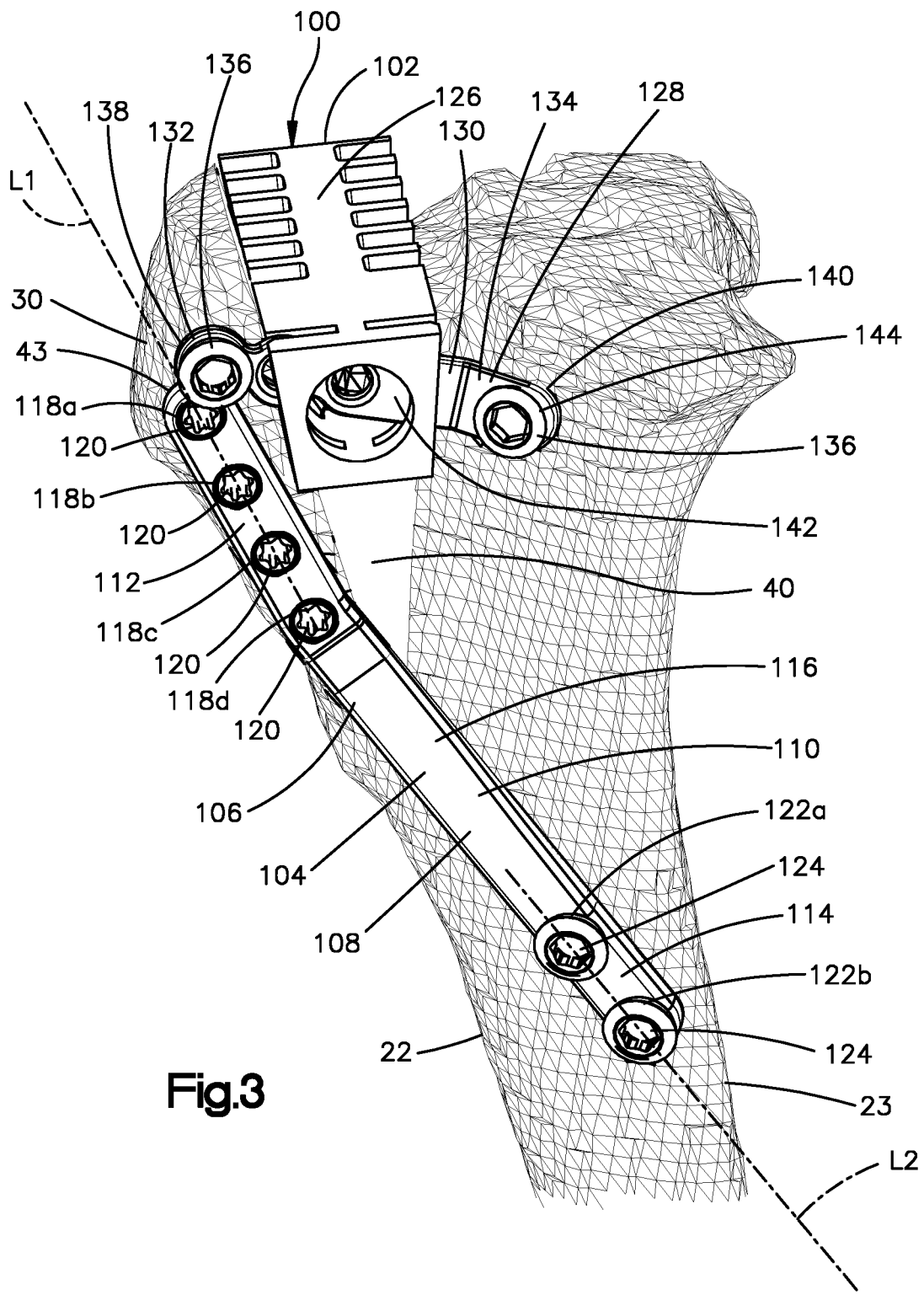
FIG. 3 is a perspective view of at least part of a Tibial Tuberosity Advancement (TTA) system in accordance with an embodiment of the present disclosure, the TTA system including a spacer, a spacer fixation member, and an implant.

With reference to FIG. 3, a Tibial Tuberosity Advancement (TTA) system 100 can be configured to stabilize cranial cruciate ligament-deficient stifles in quadrupeds. In one embodiment, the TTA system 100 includes an implant 104, such as a tibial tuberosity advancement (TTA) implant, for a quadruped. The implant 104 can be constructed as a bone fixation member 106, such as a bone plate 108. In the depicted embodiment, the implant 104 includes an implant body 110 that includes a proximal end portion 112, an opposed distal end portion 114, and an intermediate implant portion 116 disposed between the proximal end portion 112 and the distal end portion 114.

Figure 1:
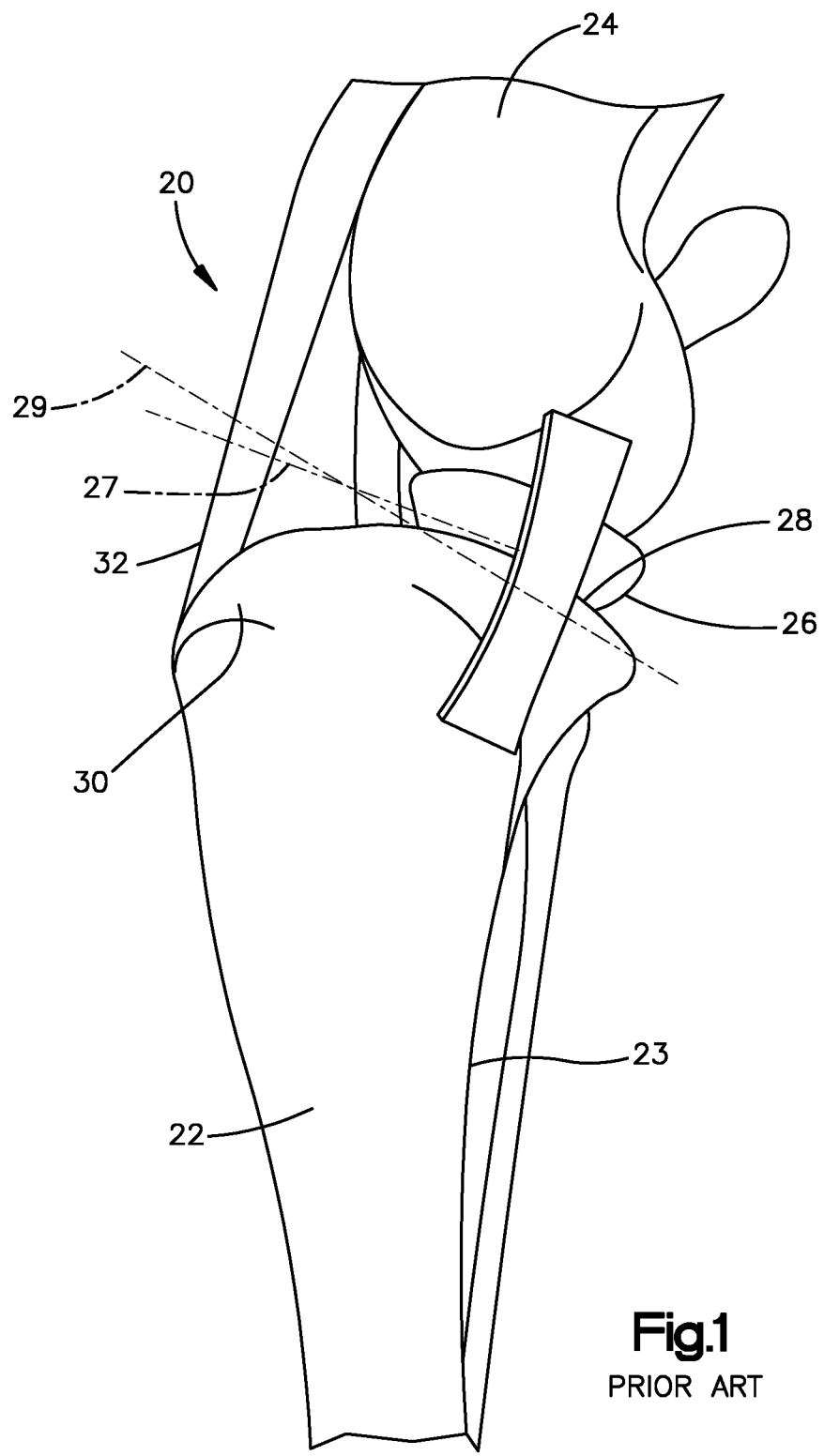
FIG. 1 is an illustration of a healthy knee of a canine.
Figure 2:
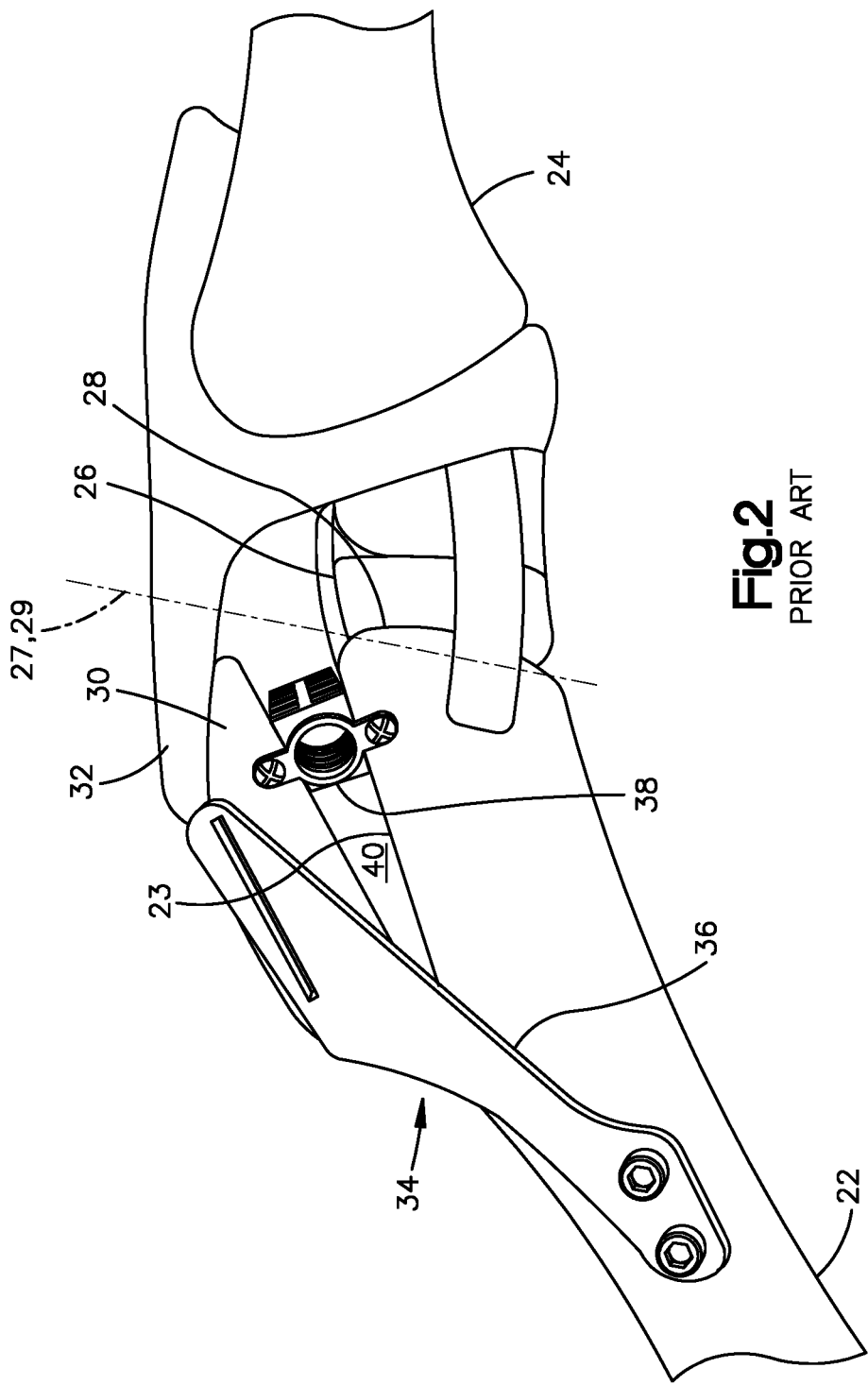
FIG. 2 is a side elevation view of a conventional tibial tuberosity advancement system implanted in the knee illustrated in FIG. 1, for instance in response to an injury to the cranial cruciate ligament of the knee.

The proximal end portion 112 of the implant body 110 can be configured to be attached to the tuberosity 30 that has been advanced along with the patellar tendon 32 (shown in FIG. 1) in a direction cranially relative to the tibial body 23 from a first position to an advanced position. The distal end portion 114 of the implant body 110 can be configured to be attached to the tibial body 23. It should be appreciated that the patellar tendon 32 is attached to the tuberosity 30 at an anatomical attachment location 43, and that the tuberosity 30 can be resected, and thus separated, from the tibial body 23 at a location caudal of the attachment location 43 such that the patellar tendon 32, including the attachment location 43, is advanced along with the separated tuberosity 30 from the first position to the advanced position. The proximal end portion 112, the distal end portion 114, and the intermediate implant portion 116 can collectively be a monolithic structure. Alternatively, proximal end portion 112, the distal end portion 114, and the intermediate implant portion 116 can be discrete components that are connected to each other to form the implant body 110.

The proximal end portion 112 can be contoured and configured to conform to a medial surface or lateral surface of the tuberosity 30 to facilitate attachment of the implant 104 to the tuberosity 30. Moreover, the proximal end portion 112 includes one or more attachment locations such as fastener holes. In the depicted embodiment, the proximal end portion 112 of the implant body 110 includes four fastener holes 118a, 118b, 118c, and 118d. However, the proximal end portion 112 may include more or fewer fastener holes. Irrespective of the specific number of fastener holes, each fastener hole 118a, 118b, 118c, and 118d extends through the implant body 110, and is configured and sized to receive a fastener 120, such as a bone anchor, that is capable of attaching the implant 104 to the tuberosity 30.

Examples of suitable fasteners 120 include, but are not limited to, bone screws, nails, pins, and any other apparatus that is configured to attach the implant 104 to the tuberosity 30. For instance, the fastener holes 118a, 118b, 118c, and 118d can be threaded holes that are configured to receive a bone screw. Furthermore, the fasteners holes 118a, 118b, 118c, and 118d can be conical thread holes that are configured receive bone screws with a threaded conical head. The insertion of fasteners 120 through fastener holes 118a, 118b, 118c, and 118d causes the proximal end portion 112 to be attached to the tuberosity 30. The fastener holes 118a, 118b, 118c, and 118d may be spaced apart from one another and substantially aligned along a first longitudinal axis L1 that extends substantially parallel to the direction of elongation of the tuberosity 30 when the implant 104 is attached to the advanced tuberosity 30. In one embodiment the proximal end portion 112 can be elongate along the longitudinal axis L1.

The distal end portion 114 can be contoured and configured to conform to a medial surface or a lateral surface of the tibial body 23 to facilitate attachment of the implant 104 to the tibial body 23. Further, the distal end portion 114 of the implant body 110 can include one or more anchor locations such as fastener holes. In the depicted embodiment, the distal end portion 114 includes a first fastener hole 122a and a second fastener hole 122b. Each of the fastener holes 122a and 122b can be configured and sized to receive a fastener 124, such as a bone anchor, capable of attaching the implant 104 to the tibial body 23.

Examples of suitable fasteners 124 include, but are not limited to, bone screws, nails, pins, and any other apparatus that is configured to attach the implant 104 to the tibial body 23. The insertion of fasteners 124 through the fastener holes 122a and 122b causes the distal end portion 114 to be attached to the tibial body 23. The fastener holes 122a and 122b may be spaced apart from one another and substantially aligned along a second longitudinal axis L2. In one embodiment the distal end portion 114 can be elongate along the second longitudinal axis L2. The second longitudinal axis L2 may be angularly offset from the first longitudinal axis L1.

The intermediate implant portion 116 of the implant body 110 can be elongated along the second longitudinal axis L2. Alternatively, the intermediate implant portion 116 may be elongated along an axis that is angularly offset from the second longitudinal axis L2. Although the drawings do not show attachment locations, such as fastener holes, in the intermediate implant portion 116, it is envisioned that the intermediate implant portion 116 may include one or more fastener holes or any other suitable attachment feature. The intermediate implant portion 116 extends between the proximal end portion 112 and the distal end portion 114 and is shaped so as to space the proximal end portion 112 cranially with respect to the distal end portion 114 an amount, or a distance, sufficient so as to maintain the tuberosity 30 in the advanced position.

The TTA system 100 can further include a spacer 102 configured to maintain a distance between the tibial body 23 and the tuberosity 30 when the tuberosity 23 is in the advanced position. The spacer 102 can be configured and sized to at least partially fit in the osteotomy gap 40 defined between the tibial body 23 and the advanced tuberosity 30. In the depicted embodiment, the spacer 102 can be configured as a cage 126 as described in detail below.

Aside from the spacer 102, the TTA system 100 can include a spacer fixation member 128 that is configured to couple the spacer 102 to the tibial body 23 and the advanced tuberosity 30, thereby fixing the spacer 102 in the osteotomy gap 40. As discussed in detail below, the spacer fixation member 128 can be configured as a bone plate 130. At least a portion of the bone plate 130 can be configured and sized to be inserted through the spacer 102. The spacer fixation member 128 includes a body 134, which is also referred to as a plate body. The body 134 of the spacer fixation member 128 can be elongated, and can define first end portion 138, a second end portion 140, and an intermediate fixation portion 142 (shown in FIG. 5A) disposed between the first end portion 138 and the second end portion 140.

The first end portion 138 can be configured to be attached to the advanced tuberosity 30. To this end, the first end portion 138 can be contoured and configured to conform to a lateral surface or a medial surface of the advanced tuberosity 30, and can include one or more attachment locations such as fastener holes 132. The fastener holes 132 can be configured and sized to receive a fastener 136, such as a bone anchor, capable of attaching the spacer fixation member 128 to the advanced tuberosity 30. Suitable fasteners 136 include, but are not limited to, bone screws, nails, pins, or any other fastener 136 that can attach the first end portion 138 to the advanced tuberosity 30.

The second end portion 140 of the body 134 is configured to be attached to the tibial body 23. To this end, the second end portion 140 can be contoured and configured to conform to a lateral surface or a medial surface of the tibial body 23, and can include one or more attachment locations such as fastener holes 144. In the depicted embodiment, the second end portion 140 includes only one fastener hole 144; however, it is envisioned that the second end portion 140 can define more than one fastener hole 144. The fastener hole 144 can be configured and sized to receive a fastener 136, such as bone anchors. Examples of fasteners 136 include, but are not limited to, bone screws, nails, pins or any other apparatus that can attach the second end portion 140 to the tibial body 23.

The intermediate fixation portion 142 is configured to be inserted through an opening, such as a slot, of the spacer 102 in order to secure the spacer 102 in the osteotomy gap 40 when the first end portion 138 is attached to the advanced tuberosity 30 and the second end is attached to the tibial body 23. In the depicted embodiment, the intermediate fixation portion 142 can have a substantially planar configuration as described in detail below. The first end portion 138, the second end portion 140, and the intermediate fixation portion 142 can be a monolithic structure. Alternatively, the first end portion 138, the second end portion 140, and the intermediate fixation portion 142 can be discrete components connected to one another. The intermediate fixation portion 142 can define a substantially planar configuration that is configured to fit within a slot of the spacer 102 as discussed below.

With reference to FIGS. 4A-4E, the spacer 102 can include a spacer body 148 configured and sized to fit in the osteotomy gap 40. The spacer body 148 can be elongate along a longitudinal direction 150, and can define a first longitudinal end 152 and a second longitudinal end 154 that is spaced from the first longitudinal end 152 along the longitudinal direction 150. Furthermore, the spacer body 148 defines a first lateral end 156 and a second lateral end 158 that is spaced from the first lateral end 156 along a lateral direction 160. The lateral direction 160 is substantially perpendicular to the longitudinal direction 150.

Specifically, the spacer body 148 may have a first transverse end 164 and a second transverse end 166 that is spaced from the first transverse end 164 along the transverse direction 162. The transverse direction 162 is substantially perpendicular to the longitudinal direction 150 and the lateral direction 160. In the depicted embodiment, the spacer body 148 can define a substantially partial wedge shape such that its width increases in the transverse direction 162. The width of the spacer body 148 is defined between the first lateral end 156 and the second lateral end 158. In the depicted embodiment, the spacer body 148 can define a first width W1 at the first transverse end 164 that is greater than a second width W2 at the second transverse end 166. The wedge-shape of the spacer body 148 facilitates insertion and positioning of the spacer 102 in the osteotomy gap 40 since the osteotomy gap 40 has a substantially wedge shape.

The spacer 102 can further include an opening 168 that extends through spacer body 148 from the first longitudinal end 152 to the second longitudinal end 154. Thus, the opening 168 can be elongate along the longitudinal direction 150. The opening 168 can be constructed as a hole, and is configured to receive bone graft or any other natural or synthetic material capable of promoting bone growth. However, the opening 168 does not necessarily have to be filled with a bone graft or any other bone growth agent. The opening 168 provides an open space to permit natural bone growth when the spacer 102 is disposed in the osteotomy gap 40. During natural bone growth, the natural bone can grow and fill at least a portion of the opening 168 when the spacer 102 is disposed in the osteotomy gap 40.

The spacer 102 further defines a first slot 170 that extend through the spacer body 148 from the first lateral end 156 to the second lateral end 158. Hence, the first slot 170 can be elongate along the lateral direction 160. The first slot 170 is located closer to the first longitudinal end 152 than to the second longitudinal end 154, and is configured and sized to receive at least a portion of the spacer fixation member 128 so as to couple the spacer 102 to the spacer fixation member 128. In the depicted embodiment, the first slot 170 can define a plane that is substantially normal to the longitudinal direction 150. The intermediate fixation member 142 can have a substantially planar configuration so that it is configured to fit within the slot 170 of the spacer 102, thereby coupling the spacer 102 to the spacer fixation member 128.

In addition to the first slot 170, the spacer 102 includes at least one second slot 172 that extends through the spacer body 148 from the first lateral end 156 to the second lateral end 158. In the depicted embodiment, the spacer 102 defines a plurality of second slots 172 that are spaced from each other along the longitudinal direction 150. At least one of the second slots 172 is located closer to the second longitudinal end 154 than to the first longitudinal end 152. Each of the second slots 172 defines a plane that is oriented at an oblique angle relative to the longitudinal direction 150. In use, the second slots 172 configured to receive bone graft or any other natural or synthetic material capable of promoting bone growth. The second slots 172 do not necessarily have to be filled with a bone graft or any other bone growth agent. Rather, the second slots 172 provide an open space to permit natural bone growth when the spacer 102 is disposed in the osteotomy gap 40.

During natural bone growth, the natural bone can grow and fill at least a portion of the second slots 172 when the spacer 102 is disposed in the osteotomy gap 40. The second slots 172 also facilitate cutting the spacer 102. As discussed in detail below, the spacer 102 can be cut to decrease its length 174, which is defined by the distance between the first longitudinal end 152 and the second longitudinal end 154 along the longitudinal direction 150. In operation, the length 174 of the spacer 102 may have to be shortened so that the spacer 102 can properly fit in the osteotomy gap 40. For this purpose, each of the second slots 172 can be configured and sized to receive at least a portion of a cutting tool, such as a saw. In operation, the saw can be inserted through one of the slots 172 to cut the spacer 102, thereby shortening its length 174. The spacer 102 can also be partly or entirely made of a material that can be cut with a cutting tool such as a saw. The spacer 102 can also include a plurality of tines 173. At least some of the tines 173 are disposed between two slots 172. The tines 173 can have a substantially planer configuration. In the depicted embodiment, the tines 173 are obliquely angle relative to the longitudinal direction 150. The spacer 102 can be partly or entirely made of any suitable biocompatible material such as polyetheretherketone (PEEK).

With reference to FIGS. 4F-L, the TTA system 100 can be part of a kit that includes spacers of different sizes. Thus, the kit may include spacers with different lengths, heights, and width. For example, the kit may include spacers 102a, 102b, 102c, 102d, 102e, 102f, and 102g. Except for their dimensions, the spacers 102a, 102b, 102c, 102d, and 102e are substantially similar to the spacer 102 described above with respect to FIGS. 4A-E. Thus, the spacers 102g and 102f are substantially similar to the spacer 102 described above with respect to FIGS. 4A-E; however, due to size restrictions, spacers 102g and 102f do not include an opening like the opening 168 of the spacer 102. Moreover, the spacers 102g and 102f are smaller than the spacer 102 described above with respect to FIGS. 4A-E.

With reference to FIG. 5A, the spacer fixation member 128 is configured to couple the spacer 102 to the tibial body 23 and the advance tuberosity 30 in order to secure the spacer 102 in the osteotomy gap 40. In the depicted embodiment, the spacer fixation member 128 can be configured as the bone plate 130, and includes a body 134 that configured and sized to partially fit within the first slot 170 of the spacer 102. The body 134 can also be referred to as the plate body. Furthermore, the body 134 can define the first end portion 138, the second end portion 140, and the intermediate fixation portion 142 disposed between the first end portion 138 and the second end portion 140.

The first end portion 138 can be elongate along a longitudinal axis 176, and can configured to be attached to the advanced tuberosity 30. To facilitate attachment between the spacer fixation member 128 and the advanced tuberosity 30, the first end portion 138 can be contoured and configured to conform to a lateral surface or a medial surface of the advanced tuberosity 30, and can include one or more attachment locations such as fastener holes 132. The fastener holes 132 can be configured and sized to receive the fastener 136 as discussed above. In the depicted embodiment, the first end portion 138 defines a plurality of fastener holes 132. The plurality of fastener holes 132 allows a user to attach the spacer fixation member 128 to the advanced tuberosity 30 at different attachment locations along the first end portion 138. It is contemplated, however, that the first end portion 138 may define only one fastener hole 132.

The intermediate fixation portion 142 can be elongate along the longitudinal axis 176 and can define at least one fastener hole 178 that is configured to receive a fastener such as a bone anchor. If necessary, the spacer fixation member 128 can be cut to shorten it, and a fastener can be inserted through the fasteners hole 178 and into the tibial body 23 to couple the spacer fixation member 128 to the tibial body 23. As discussed above, at least part of the intermediate fixation portion 142 can configured to be inserted in the first slot 170 so as to couple the spacer fixation member 128 to the spacer 102.

The second end portion 140 can be elongate along a longitudinal axis 178 that is angularly offset relative to the longitudinal axis 176. In an embodiment, the second end portion 140 can be contoured and configured to conform to a lateral or medial surface of the tibial body 23. To facilitate attachment between the spacer fixation member 128 and the tibial body 23, the second end portion 140 can include one or more attachment locations such as the fastener hole 144. In the depicted embodiment, the second end portion 140 define only one fastener hole 144. However, the second end portion 140 may include more than one fastener hole 144. As discussed above, a fastener can be inserted through the fastener hole 144 and into the tibial body 23 to couple the spacer fixation member 128 to the tibial body 23.

With reference to FIG. 5B, another embodiment of the spacer fixation member 128a is substantially similar to the spacer fixation member 128 described above with respect to FIG. 5A. However, in this embodiment, the second end portion 140a includes a first section 141a that is connected to the intermediate fixation portion 142a and elongate along a longitudinal axis 177a. The longitudinal axis 177a may be substantially perpendicular to the longitudinal axis 176a. The second end portion 140a further includes a second section 143a that is elongated along a longitudinal axis 179a. The longitudinal axis 179a may be angularly offset relative to the longitudinal axis 177a and the longitudinal axis 176a. In operation, the second end portion 140a of the spacer fixation member 128a can be contoured and configured to conform to a lateral surface or a medial surface of the tibial body 23 to facilitate the connection of the spacer fixation member 128a to that lateral or medial surface.

With reference to FIGS. 6A-6C, a spacer 202 in accordance with another embodiment can be positioned in the osteotomy gap 40 to maintain the tuberosity 30 in the advanced position relative to the tibial body 23. The spacer 202 can include a spacer body 248 that can be partly or entirely made of a polyetheretherketone (PEEK) or any other suitable material. The spacer body 248 defines an upper surface 203 and an opposed lower surface 205. The upper surface 203 is spaced from the lower surface along a transverse direction 262. The spacer body 248 can include a front surface 207 and an opposed rear surface 209. The rear surface 209 can be spaced from the front surface 207 along a longitudinal direction 250. The spacer body 248 can define first lateral surface 211 and a second lateral surface 213. The second lateral surface 213 can be spaced from the first lateral surface 211 along a lateral direction 260.

The spacer 202 further defines a plurality of slots 272 that extend into the lower surface of the spacer body 248. The slots 272 can be spaced apart from one another along the lateral direction 260. Each of the slots 272 can be elongate along the transverse direction 262. Moreover, each of the slots 272 can extend through the spacer body 248 from the front surface 207 to the rear surface 209. When the spacer 202 is disposed in the osteotomy gap 40, the slots 272 provide an open space to permit bone growth. The slots 272 also facilitate cutting of the spacer 202 in order to shorten its length. In addition, any suitable natural or synthetic bone growth material can be disposed in the slots 272 to promote bone growth when the spacer 202 is disposed in the osteotomy gap 40. The slots 272 also facilitate cutting of the spacer 202. As discussed above, the spacer 202 may be cut if necessary to properly fit in the osteotomy gap 40. For instance, a cutting tool can be inserted through one of the slots 272 to cut the spacer 202, thereby shortening the spacer 202 along the lateral direction 260.

The spacer body 248 can include a plurality of resilient tines 275 that are spaced from one another along the lateral direction 260. Each resilient tine 275 is disposed between two slots 272. The resilient tines 275 allows the spacer body 248 to be compressed along the lateral direction 260 when the spacer 202 is disposed in the osteotomy gap 40 so as to allow at least a portion of the spacer body 248 to conform to the shape of the osteotomy gap 40. The resilient tines 275 may also have different lengths so as to define an arch-shaped bottom lower surface 205. In particular, the resilient tines 275 may define a concave lower surface 205 that allows the tines 275 to be compressed against one another so as to conform to the shape of the osteotomy gap 40 when the spacer 202 is disposed in the osteotomy gap 40.

The spacer 202 can further include one or more holes 270 that into the spacer body 248 along the lateral direction 260. In the depicted embodiment, the holes 270 extend through the spacer body 248 from the first lateral surface 211 to the second lateral surface 213 along the lateral direction 260. When the spacer 202 is disposed in the osteotomy gap 40, the holes 270 provide an open space to promote bone growth. In addition to the holes 270, the spacer 202 may define one or more ridges 273 that extend into the upper surface 203. In the depicted embodiment, the ridges 273 can be spaced from one another along the lateral direction 260. The ridges 273 can be elongate along the longitudinal direction 250. In operation, the cutting tool, such as a saw, can be inserted in one of the ridges 273 to cut the spacer 202. Thus, the ridges 273 facilitate cutting of the spacer 202. The ridges 273 also permit the spacer 202 to flex.

The spacer 202 can further define at least one fastener hole 215 that is configured and sized to receive a fastener 133. The fastener 133 can be configured to couple the spacer fixation member 128a (or any other spacer fixation member) to the spacer 202. In the depicted embodiment, the fastener 133 is configured as a screw, and the fastener hole 215 can be a threaded hole. It is envisioned, however, that the fastener 133 can be configured as a nail, a pin, or any other apparatus configured to couple the spacer fixation member 128a to the spacer 202. To couple the spacer fixation member 128a to the spacer 202, the fastener 133 can be inserted through one of the fastener holes 132a of the spacer fixation member 128a and into the fastener hole 215. As discussed above, the spacer fixation member 128a can also be coupled to the advanced tuberosity 30 and the tibial body 23 via fasteners.

Figure 7A:
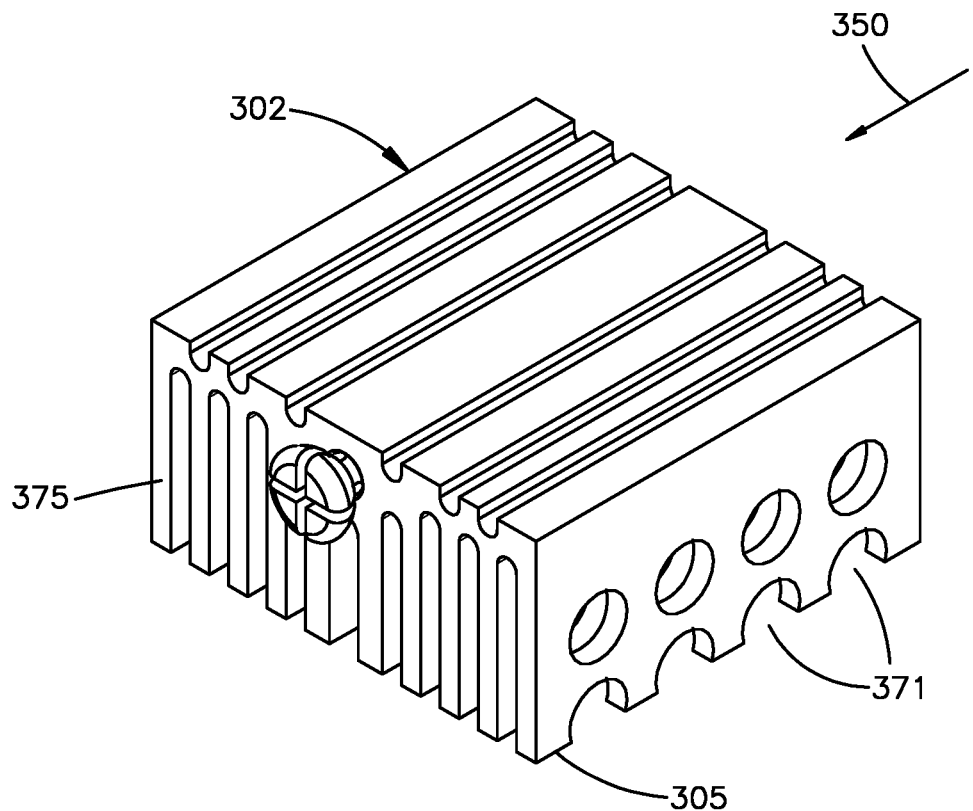
FIG. 7A is a perspective view of a spacer in accordance with one embodiment and a fastener.
Figure 7B:
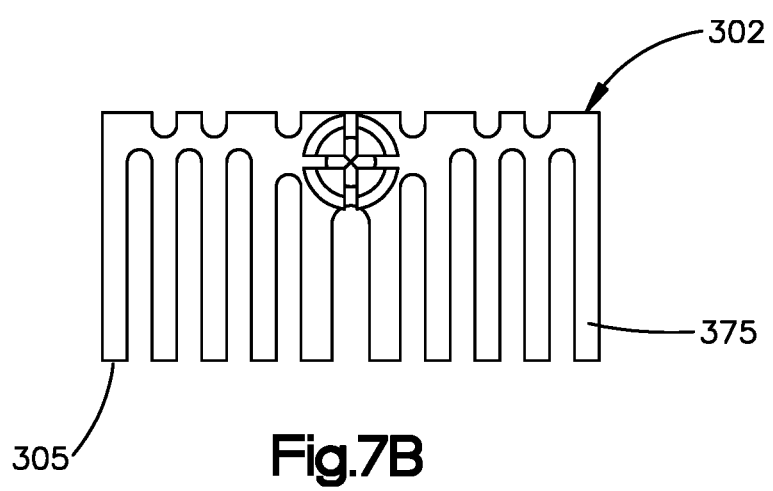
FIG. 7B is a front elevation view of the spacer and the fastener shown in FIG. 7A.

With reference to FIGS. 7A-B, a spacer 302 in accordance with another embodiment can be positioned in the osteotomy gap 40 to maintain the tuberosity 30 in the advanced position relative to the tibial body 23. The spacer 302 is substantially similar to the spacer 202. However, in this embodiment, the resilient tines 375 have substantially similar or identical lengths and, therefore, do not define a concave lower surface 305. Instead, the lower surface 205 may have a substantially planar configuration. Moreover, the spacer 302 can further define recesses 371, such as partial holes, that extend into the lower surface 305. The recesses 371 can be spaced from one another along the longitudinal direction 350. In operation, the recesses 371 provide an open space to permit bone growth when the spacer 302 is disposed in the osteotomy gap 40.

Figure 8B:
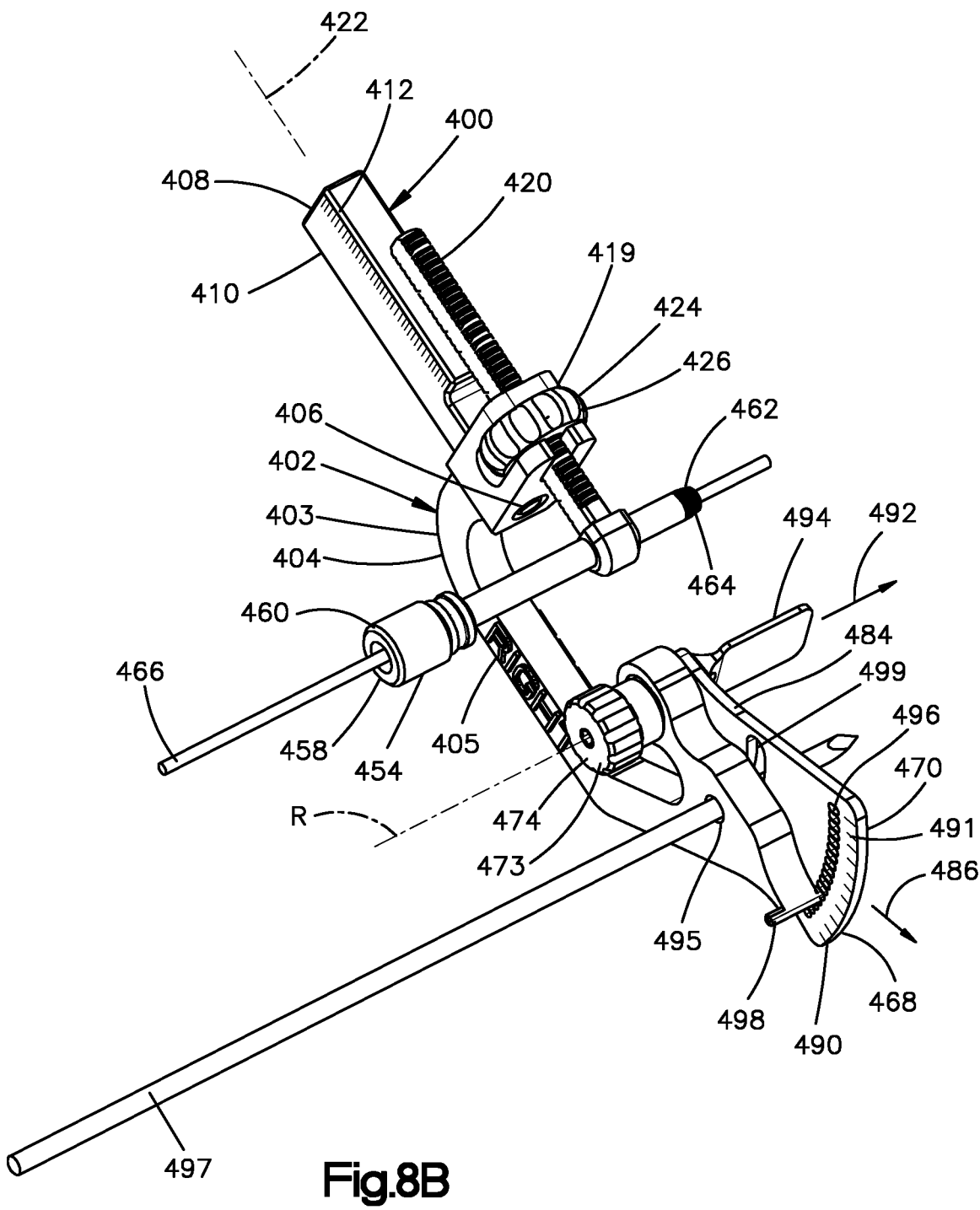
FIG. 8B is a perspective view of the guide assembly shown in FIG. 8A.
Figure 8C:
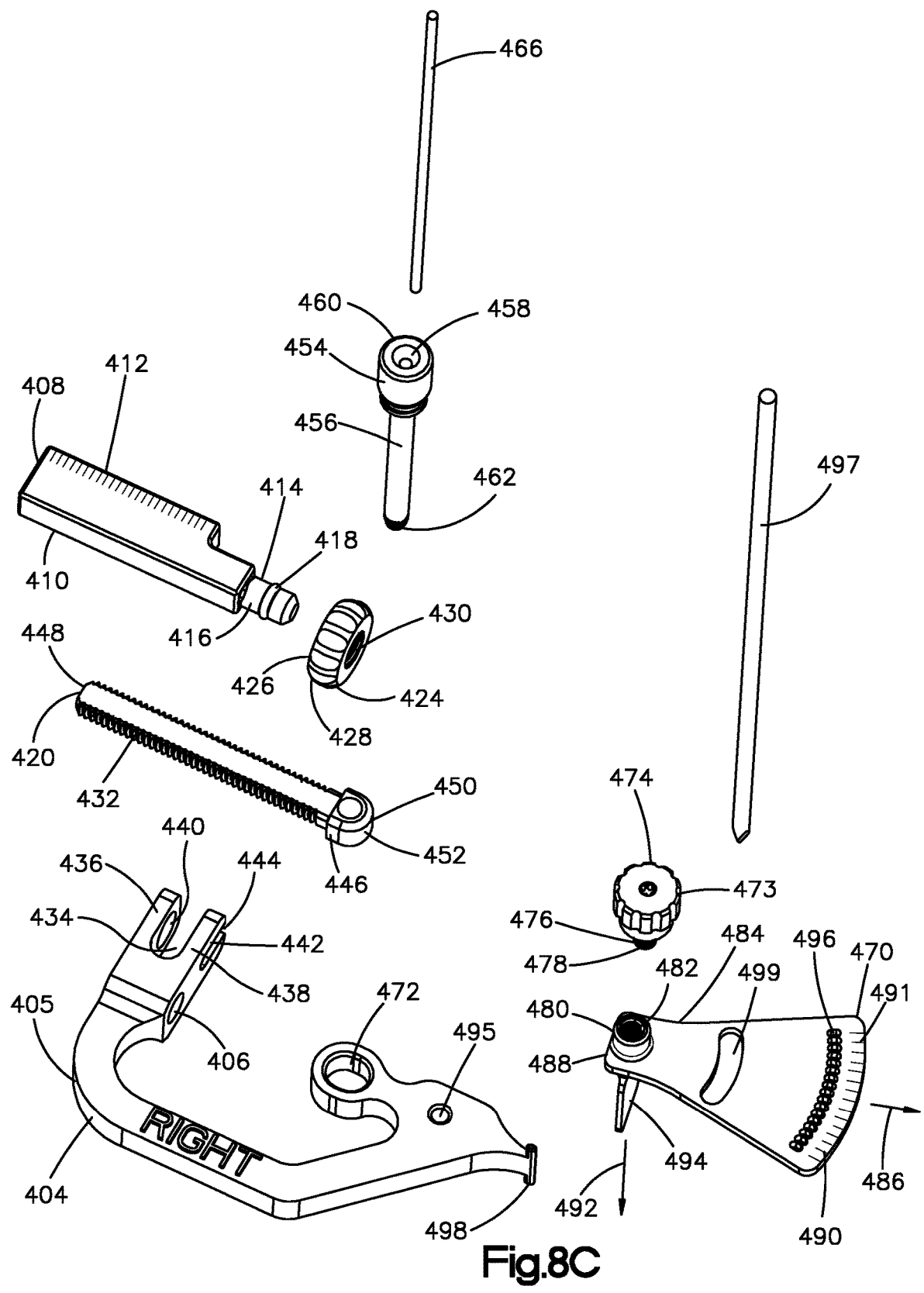
FIG. 8C is a perspective exploded view of the guide assembly shown in FIG. 8A.

With reference to FIGS. 8A-C, the TTA system 100 can also include a TTA advancement assembly 400 configured to guide the advancement of the tuberosity 30 relative to the tibial body 23. As discussed in detail below, the advancement assembly 400 can be used to advance the tuberosity 30 relative to the tibial body 23 is described in detail below. The advancement assembly 400 includes an advancement member 402 that is configured to be coupled to the implant 104, which in turn is coupled to the tuberosity 30. Specifically, the advancement member 402 can be coupled to the proximal end portion 112 of the implant 104. In the depicted embodiment, the advancement member 402 can be coupled to the implant 104 at the attachment location defined by the fastener hole 118a. The implant 104 can be attached to the tuberosity 30 and the advancement member 402. Therefore, the advancement member 402 can be manipulated to advance the tuberosity 30 (via implant 104) relative to the tibial body 23.

With continuing reference to FIGS. 8A-C, the advancement member 402 can be configured as a jig 403, and can include an advancement body 404. The advancement body 404 can be configured as a jig body or a frame. Regardless of its configuration, the advancement body 404 defines an attachment location such as a displacement scale hole 406 that is configured to securely receive a displacement scale 408. Thus, the advancement assembly 400 can include a displacement scale 408 that can be used to measure the longitudinal displacement of the tuberosity 30 relative to the tibial body 23. The displacement scale 408 can be removably attached to the advancement body 404 via the displacement scale hole 408.

The displacement scale 408 includes a body 410 that includes measurement markings 412 that can be used to measure the longitudinal displacement of the tuberosity 30 relative to the tibial body 23. In addition to the body 410, the displacement scale 408 includes a connection member 414 that protrudes from the body 410. The connection member 414 can be configured as a substantially cylindrical body, and can be removably disposed in the displacement scale hole 406. The connection member 414 can include a connection body 416 and a ring 418 disposed around the connection body 416. The connection body 416 is configured and sized to be at least partially received in the displacement scale hole 406. When the connection member 414 is at least partially disposed in the displacement scale hole 406, the ring 418 abuts the inner surface of the advancement body 404 that defines the displacement scale hole 406, thereby establishing a friction fit connection between the connection member 414 and the advancement body 404.

The advancement assembly 400 can further include a longitudinal distraction mechanism 419 that is configured to move the tuberosity 30 relative to the tibial body 23 when the advancement assembly 400 is coupled to the tuberosity 30 and the tibial body 23. In the depicted embodiment, the distraction mechanism 419 can include a distraction arm 420 that is movably coupled to the advancement body 404, and an actuator 424 such as a knob 426. In operation, the distraction arm 420 is configured to move relative to the advancement body 404 upon actuation of the actuator 424. Thus, the actuation of the actuator 424 causes the distraction arm 420 to move relative to the advancement body 404 along a longitudinal distraction axis 422. In operation, the movement of the distraction arm 420 relative to the advancement body 404 causes the tuberosity 30 to move relative to the tibial body 23 when the advancement assembly 400 is coupled to the to the tuberosity 30 and the tibial body 23.

As discussed above, the actuator 424 can be configured as a knob 426. The knob 426 can include a knob body 428, and can define a threaded hole 430 that is configured and sized to receive at least a portion of the distraction arm 420. The threaded hole 430 can extend through the knob body 428. The distraction arm 420 can include external threads 432 that are configured to mate with the inner threads disposed around the threaded hole 430 such that rotation of the knob 426 about the distraction arm 420 causes the distraction arm 420 to move relative to the knob 426 along the longitudinal distraction axis 422. Hence, the distraction arm 420 can be configured to move relative to the advancement body 404 upon rotation of the knob 426. While the distraction arm 420 can move longitudinally relative to the advancement body 404, the knob 426 is fixed longitudinally with respect to the advancement body 404.

The advancement member 402 can include a first attachment prong 436 and a second attachment prong 438 that are spaced apart from each other so as to define a knob channel 434. The first attachment prong 436 and the second attachment prong 438 can protrude from the advancement body 404. The knob channel 434 can be configured and sized to receive the knob 426 so as to longitudinally fix the knob 426 to the advancement member 402 while allowing the knob 426 to rotate within the knob channel 434. The knob 426 can be configured to rotate about the longitudinal distraction axis 422. The first attachment prong 436 defines a distraction arm hole 440 that is configured to receive at least a portion of the distraction arm 420. The distraction arm 402 can slide through the distraction arm hole 440. The second attachment prong 438 can define a distraction arm channel 442 that is configured and sized to receive at least a portion of the distraction arm 420. The distraction arm 420 can slide through the distraction arm channel 442. The second prong 438 can also define a first stop member 444 that is configured to abut a second stop member 446 of the distraction arm 420 so as to limit the longitudinal movement of the distraction arm 420 relative to the advancement member 402.

The distraction arm 420 can define a first end 448 and a second end 450, the second end 450, as shown in the illustrated embodiment, can in turn define the second stop member 446. The first end 448 can be spaced from the second end 450 along the longitudinal distraction axis 422. The distraction arm 420 can further define a dill guide hole 452 that extends through the second end 450 of the distraction arm 420. The drill guide hole 452 can be configured and sized to receive a drill guide 454, which can be configured as a sleeve. The drill guide 454 can include a drill guide body 456 that defines a first end 460 and a second end 462 spaced apart from each other.

The second end 462 can define a threaded tip 464 that is configured and sized to mate with the threaded fastener hole 118a (FIG. 3) of the implant 404 so as to couple the drill guide 454 to the implant 104. The threaded tip 464 can have a frusto-conical shape. The drill guide 454 can define a drill guide opening 458 that extends through the drill guide body 456 between the first end 460 and the second end 462. The drill guide opening 458 can be configured and sized to receive a drill bit or a temporary fixation member such as a wire 466. The wire 466 can be a Kirschner wire, and is configured to be inserted through the drill guide opening 458 and into the tuberosity 30 so as to couple the advancement assembly 400 to the tuberosity 30 when the drill guide 454 is coupled to the distraction arm 420.

The advancement assembly 400 can further include an angular adjustment mechanism 468 that is configured to adjust the angular position of the tuberosity 30 with respect to the tibial body 23 when the advancement assembly 400 is coupled to the tibial body 23 and the tuberosity 30. In the depicted embodiment, the angular adjustment mechanism 468 can include an angular adjustment member 470 that is movably coupled to the advancement body 404. Specifically, the angular adjustment member 470 is configured to rotate about an attachment location defined along a pivot axis R. In particular, the advancement member 402 defines an attachment location such as a hole 472. The hole 472 extends through the advancement body 404 along the pivot axis R, and is configured to receive at least a portion of a rotational actuator 474 such that the rotational actuator 474 is configured to rotate about the pivot axis R within the hole 472.

The rotational actuator 474 can be configured as a knob 473, and includes an attachment member 476 that is configured to mate with an attachment member 480 of the angular adjustment member 470 so as to couple rotational actuator 474 to the angular adjustment member 470. The attachment member 476 can be configured as an externally threaded body 478, and the attachment member 480 can be configured as a threaded hole 482. The threaded hole 482 can be configured to mate with the externally threaded body 478 so as to couple the rotational actuator 474 to the angular adjustment member 470. The angular adjustment member 470 can be configured as an angular scale.

The angular adjustment member 470 can also be angularly fixed relative to the angular body 404 by tightening the rotational actuator 474. For example, the rotation of the rotational actuator 474 about the pivot axis R in a first direction tightens the externally threaded body 478 in the threaded hole 482, thereby angularly fixing the angular adjustment member 470 with respect to the advancement body 404. Conversely, the rotation of the rotational actuator 474 in a second direction (opposite to the first direction) about the pivot axis R loosens the externally threaded body 478 disposed in the threaded hole 482, thereby allowing the angular adjustment member 470 to rotate about the pivot axis R with respect to the advancement body 404.

The angular adjustment member 470 includes an angular scale body 484 that is elongate along a longitudinal direction 486. The angular scale body 484 can have a substantially planar configuration, and defines a first scale end 488 and a second scale end 490. The second scale end 490 is spaced from the first scale end 488 along the longitudinal direction 486. The threaded hole 482 can be located at or close to the first scale end 488. The angular adjustment member 470 can further include a contact member 494 that protrudes from angular scale body 484 along a lateral direction 492. The lateral direction 492 can be substantially perpendicular to the longitudinal direction 486. The contact member 494 can have a substantially planar configuration, and is configured and sized to be disposed in the osteotomy gap 40. The contact member 494 can be a brace, a blade or any apparatus suitable to contact the tibial tuberosity 30, the tibial body 23, or both, when positioned in the osteotomy gap 40.

The angular adjustment member 470 can further include angular markings 491 disposed along the second scale end 490. The angular markings 491 help users determine the angular orientation of the contact member 494 relative to the advancement body 404. In particular, the angular markings 491 are disposed along an arc, which center is defined by the attachment member 480. The angular adjustment member 470 further includes a plurality of openings or recesses 496 disposed adjacent the angular markings 491. The openings 496 spaced from one another along an arc, which center is defined by the attachment member 480. Each of the openings 496 is configured and sized to receive a post 498 that protrudes from the advancement body 404 in the lateral direction 492. The engagement between the post 498 and each of the openings 496 allows a user to adjust the angular orientation of the angular adjustment member 470 at predetermined increments.

The angular adjustment member 470 further defines an arc-shaped opening 499 that extends through the angular scale body 484 along the lateral direction 492. The arc-shaped opening 499 can be elongate along an arc, which center is defined by the attachment member 480. In the depicted embodiment, the arc-shaped opening 499 is configured and sized to receive a temporary fixation member such as a wire 497. The wire 497 can be a Kirschner wire, and is configured to be inserted through the arc-shaped opening 499, an opening 495 of the advancement member 402, and into a portion of the tibial body 23, such as the tibial diaphysis, so as to couple the advancement assembly 400 to the tibial body 23. As discussed above, the advancement member 402 defines an opening 495 that extends through the advancement body 404 in the lateral direction 492. The opening 495 is substantially aligned with the arc-shaped opening 499, and can be configured and sized to receive the wire 497. While using the TTA system 100, the user, such as a surgeon, may observe its actions along a viewing direction 72. Thus, the user's line of sight when using the TTA system 100 extends along the viewing direction 72.

Figure 9:
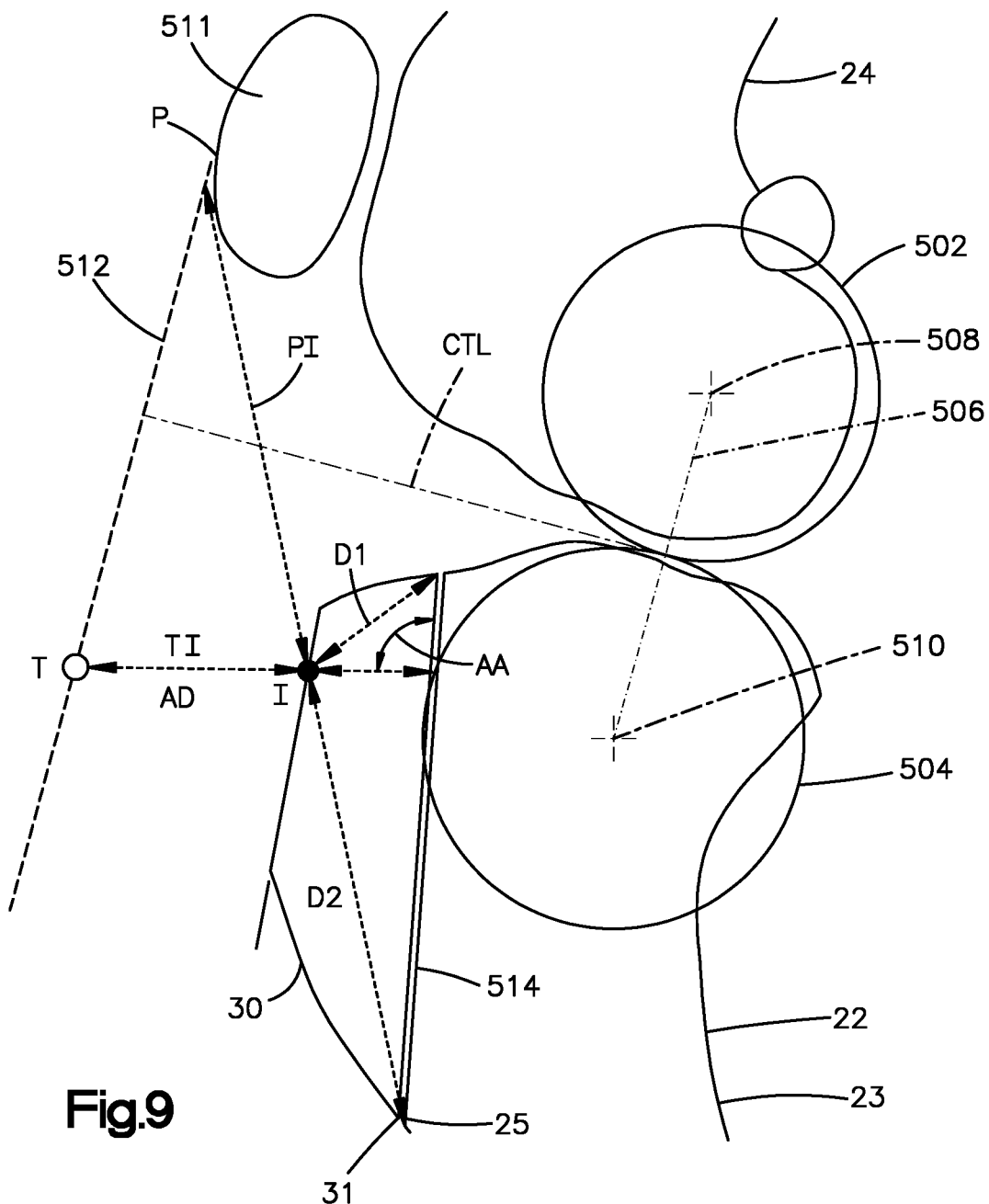
FIG. 9 is a schematic representation of a common tangent method for determining the longitudinal and angular advancement of the tuberosity relative to the tibial body.
Figure 10A:
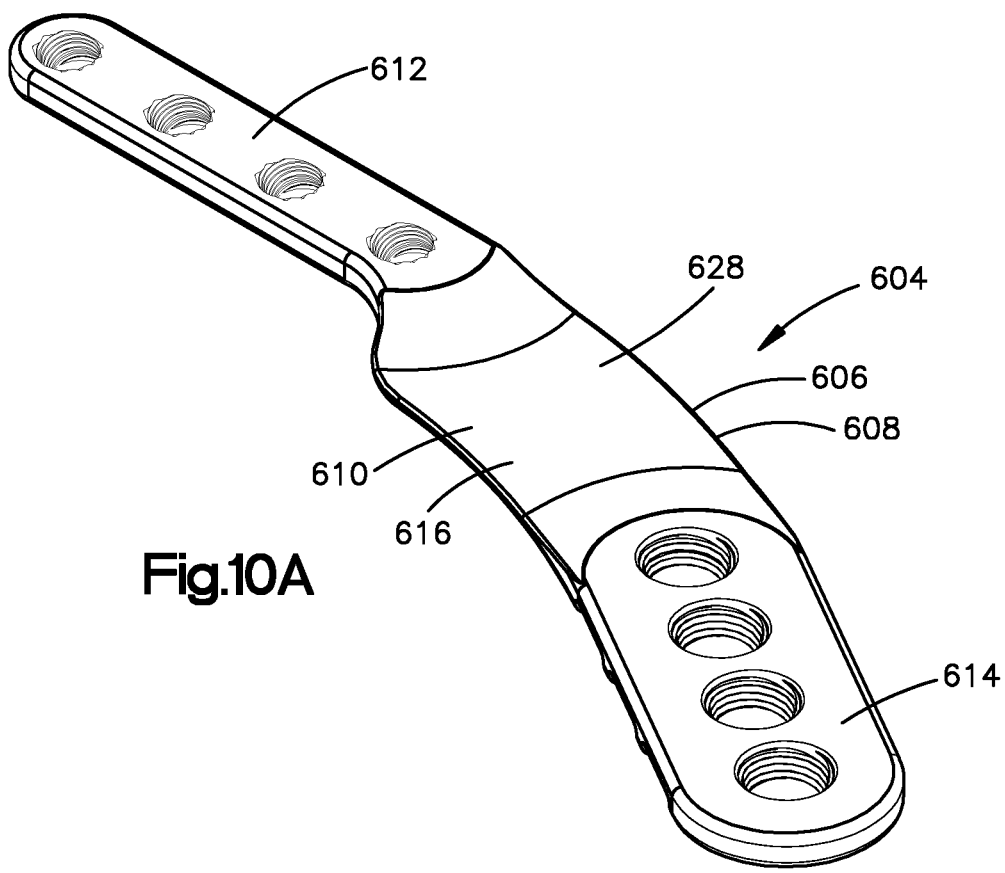
FIG. 10A is a top, rear perspective view of an implant in accordance with another embodiment.
Figure 10B:
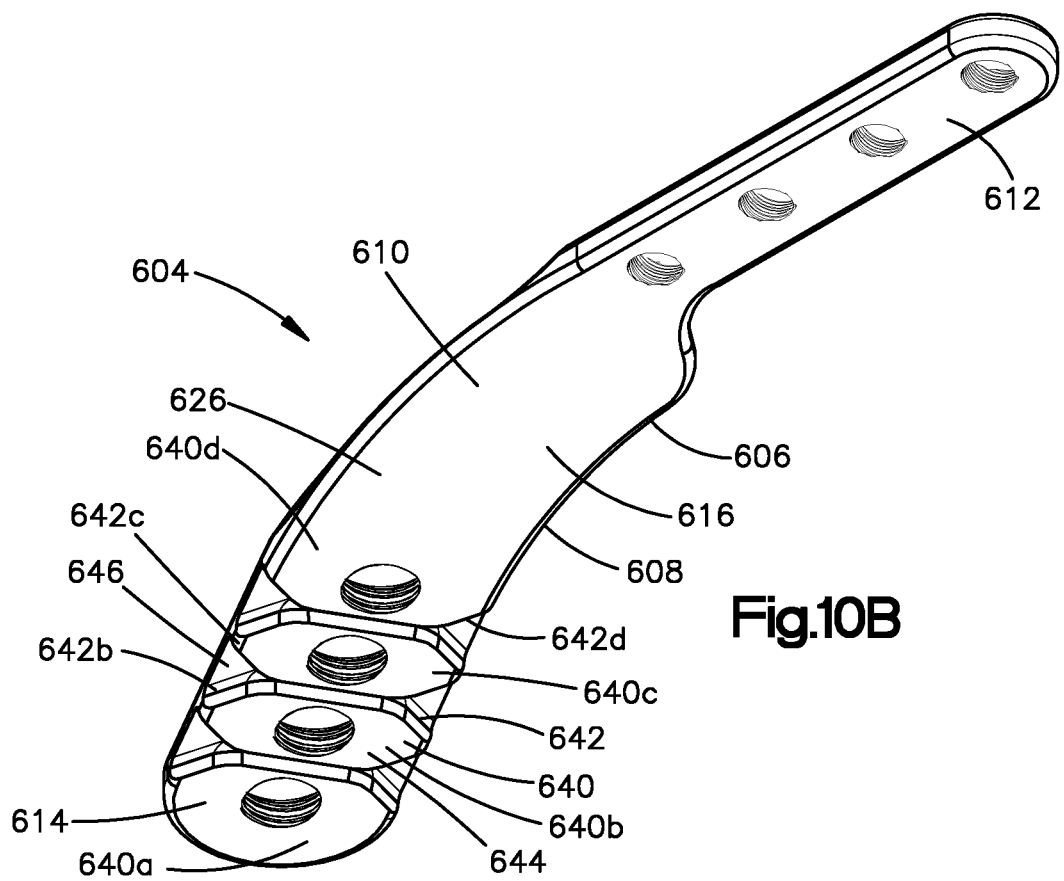
FIG. 10B is a bottom, front perspective view of the implant shown in FIG. 10A.
Figure 11A:
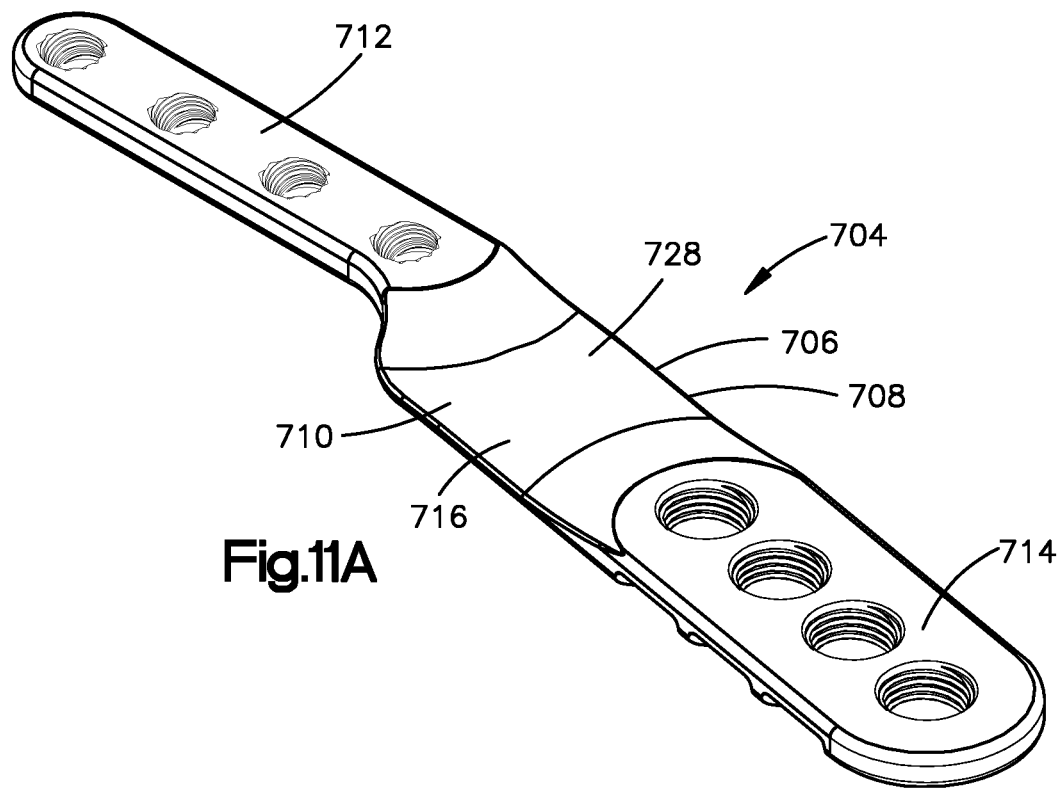
FIG. 11A is a top, rear perspective view of an implant in accordance with another embodiment.
Figure 11B:
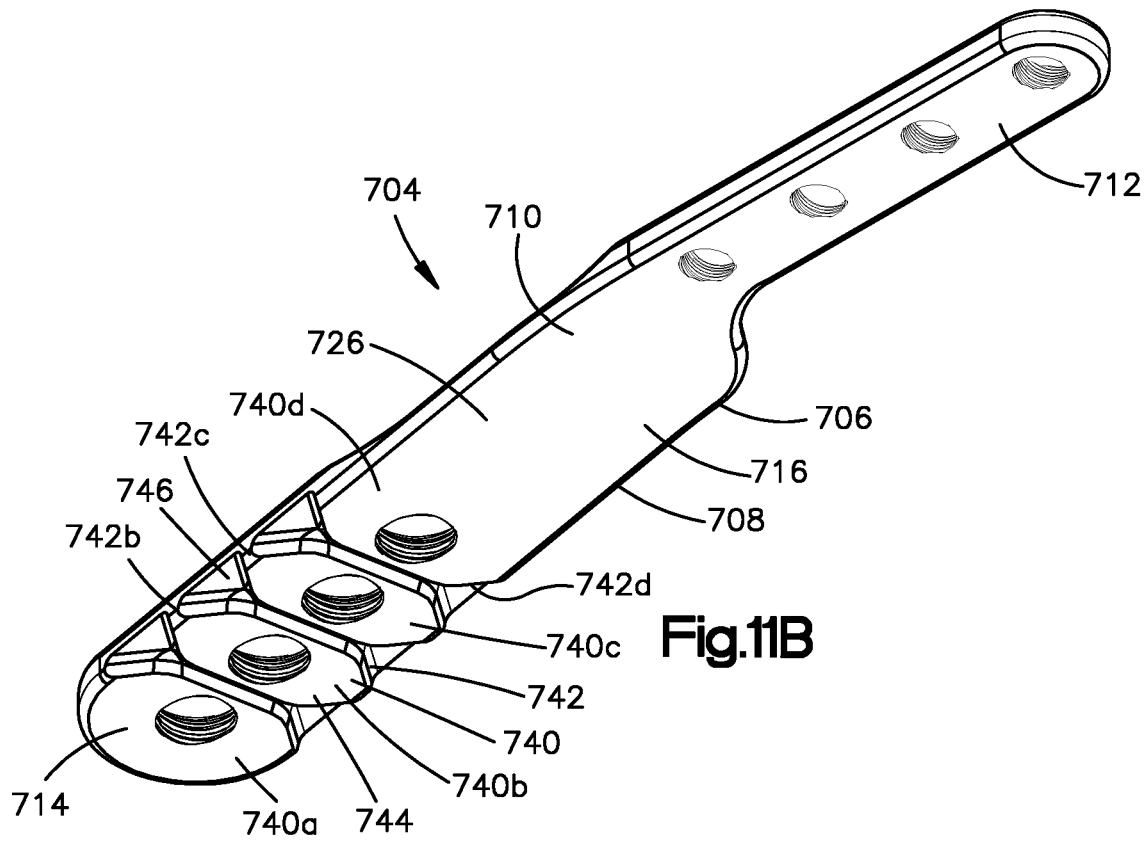
FIG. 11B is a bottom, front perspective view of the implant shown in FIG. 11A.

With reference to FIG. 9, the conventional common tangent method can be used to determine longitudinal and angular advancement of the tuberosity 30 relative to the tibial body 23. The common tangent method can be performed by a processor in a computer. Alternatively, the common tangent method can be performed by placing transparent overlays over an x-ray film. An example of the common tangent method includes all or some of the following steps. First, a first circle 502 is drawn around the articulating surface of the femur 24. A second circle 504 is drawn around the articulating surface of the tibia 22.

The first and second circles 502 and 504 should touch, for example such that the first and second circles 502 and 504 are tangent to each other. Then, a line 506 is drawn connecting the center 508 of the first circle 502 and the center 510 of the second circle 504. Next, a common tangent line CTL is drawn. The line CTL is tangential to the first circle 502 and the second circle 504 and perpendicular to the line 506. The line CTL represents the slope of the tibial plateau 28 and the direction of the cranial tibial thrust.

Next, the length of the patellar tendon 32 (shown in FIG. 1) is measured. The length of the patellar tendon 32 is defined between the distal pole P of the patella 511 wherein the patellar tendon 32 originates and the location in the tuberosity 30 where the patellar tendon 32 is inserted. The location where the patellar tendon 32 inserts into the tuberosity 30 is referred to in the present disclosure as the insertion point I. The length of the patellar tendon 32 can then be recorded as distance PI. Then, a line 512 is drawn from the distal pole P of the patella 511 to determine the target point T. The line 512 is perpendicular to the line CTL and has a length that is equal to the distance PI. The target point T is the desired location of the tuberosity 30 after the TTA procedure has been performed. That is, when the tibial tuberosity 30 is fixed at the target point T, the tibiofemoral sheer force is neutralized when weight is applied to the knee joint 20, thereby reducing or altogether bypassing the anatomical function of the CCL.

Next, the osteotomy line 514 is identified. The osteotomy line 514 can be disposed between the Gerdy's Tubercle (i.e., the lateral tubercle of the tibia) to the distal aspect of the tibial tuberosity 30. The distance D1 from the insertion point I to the most proximal end of the osteotomy line 514 is measured. A distance D2 from the insertion point I to most distal end of the osteotomy line 514 is measured. Next, a line TI is drawn from the target point T to the insertion point I. The line TI can then be extended to the osteotomy line 514. The advancement distance AD from the target point T to the insertion point I is measured. Then, the advancement angle AA is determined by measuring the acute angle between the line TI and the osteotomy line 514.

Next, in a computer, the virtual model of the implant 104 is placed over the virtual representation of the tibia 22 and femur 24 to determine the correct size of the implant 104. Alternatively, the size of the implant 104 can be determined by placing an overlay that represents the implant 104 over a radiograph of the tibia 22 and the femur 24. In this process, the proximal end portion 112 of the implant 104 should be parallel to the cranial edge of the tuberosity. Also, in this process, the fastener hole 118a should be placed at a predetermined distance (e.g., from about 1 to 2 millimeters) caudal to the insertion point I along the line TI. The steps described above can be defined as a pre-operative plan.

Upon completion of the pre-operative plan, the osteotomy may be performed. In particular, the osteotomy can be conducted from the distal aspect of the tibial tuberosity in accordance with the pre-operative plan described above. The osteotomy can be made with any suitable cutting tool. However, the osteotomy is stopped at a predetermined distance (e.g., about 3 to 4 millimeters) from the proximal cortex of the tibial tuberosity 30.

Referring to FIGS. 8A-9, after partially performing the osteotomy, the drill guide 454 is at least partially inserted through the dill guide hole 452. Then, the second end 462 of the drill guide 452 is secured in the fastener hole 118a of the implant 104 as described in detail above. The angular adjustment member 470 is then rotated relative to the advancement body 404 such that the post 498 is aligned with the marking that is equal to the predetermined advancement angle AA. The angular adjustment member 470 is then fixed relative to the advancement body 404 by tightening the rotational actuator 474 in the threaded hole 482 as described above.

The contact member 494 is inserted in the osteotomy, and then the blade is moved further into the osteotomy until the distraction arm 420 is disposed over the insertion point I as determined in the pre-operative planning. The wire 466 is then inserted through the drill guide 454 and the fastener hole 118a, and into tibial tuberosity 30 in order to secure the advancement assembly 400 and the implant 104 to the tibial tuberosity 30. The wire 466 should be oriented in the lateral direction 492. Next, the wire 497 can be inserted through the opening 495 and the arc-shaped opening 499 and into a portion of the tibial body 23, such as the tibial diaphysis, in order to secure the advancement assembly 400 to the tibial body 23. The actuator 424 is actuated to move distraction arm 420 toward the tibial body 23 in order to compress the osteotomy until a light resistance is felt. The distraction arm 420 can be moved toward the tibial body 23 by turning the knob 426 in a first direction. At this point, the user should record the starting point of the distraction arm 420 by noting the location of the first end 448 of the distraction arm 420 in relation to the markings 412 of the displacement scale 408. The implant 104 is then aligned with the cranial aspect of the tibial tuberosity 30 as determined in the pre-operative plan, and the fastener can be inserted in at least one of the fastener holes 118b, 118c, or 118d, to prevent rotation of the implant 104.

Alternatively, the advancement assembly 400 and the implant 104 can be coupled to the tibial tuberosity 30 and the tibial body 23 by performing the following steps. First, a first drill guide, which can be identical to the drill guide 454, is at least partially inserted in the fastener hole 118a so as to couple the drill guide 454 to the implant 104. The implant 104 is then placed on the tibial tuberosity 30 in accordance with the pre-operative plan. Then, the wire 466 is inserted through the drill guide 454 and into the tibial tuberosity 30, while leaving the first drill guide 454 coupled to the implant 104 and holding the implant 104 against the tibial tuberosity 30. The implant 104 is rotated so that the proximal end portion 112 of the implant 104 is substantially parallel to the cranial edge of the tuberosity.

A second drill guide, which can be identical to the drill guide 454, is then inserted through the fastener hole 118d so as to couple the second drill guide to the implant 104 at the fastener hole 118d. A drill bit can be inserted through the second drill guide and the fastener hole 118d to drill hole into the tibial tuberosity 30. A fastener, such as a locking screw, is then inserted in to the drilled hole in the tibial tuberosity 30. The angular adjustment member 470 is then adjusted at the advancement angle AA as predetermined in the pre-operative plan. The knob 473 is then tightened to fix the angular orientation of the angular adjustment member 470 with respect to the advancement body 404. The first drill guide is then decoupled from the implant 104 and withdrawn from the animal. Then, the advancement member 404 is advanced over the wire 466 such that the wire 466 is disposed in the drill guide hole 452. The distraction arm 420 can be moved away from the tibial body 23 so that the contact member 494 can be inserted in the osteotomy. The contact member 494 is then inserted in the osteotomy. Next, the wire 497 can be inserted through the opening 495 and the arc-shaped opening 499 and into a portion of the tibial body 23 such as the tibial diaphysis.

After coupling the advancement assembly 400 and the implant 104 to the tibial tuberosity 30 and the tibial body 123, the osteotomy can be completed by cutting all the way through the proximal cortex of the tibial tuberosity 30. The distraction arm 420 is then moved (via the actuator 424) away from the tibial body 23 a distance equal to the advancement distance AD. The displacement scale 408 can be used to measure the displacement of the distraction arm 420. To this end, the user can gradually turn the knob 426 in a second direction until the first end 448 of the distraction arm 420 moves a distance that is substantially equal to the advancement distance AD as measured by the markings 412. Thus, the translation of the distraction arm 420 a predetermined distance (i.e., advancement distance AD) causes the advancement assembly 400 (for example the displacement scale 408) to provide an indication that the tuberosity has advanced from the first position to the advanced position.

Then, the tibial tuberosity 30 is rotated relative to the tibial body 23 until its distal end 31 contact a surface 25 of the tibial body 23 that defines a distal end of osteotomy seen in FIG. 9. The fasteners 124 are then inserted through the fastener holes 122a and 122b and into the tibial body 23 to couple the distal end portion 114 of the implant 104 to the tibial body 23. The osteotomy gap 40 is then measured to determine the appropriate spacer size and spacer fixation member size. The spacer fixation member 128 is then coupled to the spacer 102 as described above.

Then, the spacer 102 is then inserted in the osteotomy gap 40 to verify that the appropriate size was selected. The advancement assembly 400 may be withdrawn from the animal to expand the working space. If the proper spacer 102 was selected, the spacer 102 is cut (if necessary) so that it conforms to the size of the osteotomy gap 40. The spacer 102 and the spacer fixation member 128 can then be secured in the osteotomy gap 40 by inserting the fastener 136 through the fastener holes 132 and into the tibial tuberosity 30 and by inserting another fastener 136 through the fastener holes 144 and into the tibial body 23. If the advancement assembly 400 has not been removed from the animal yet, the advancement assembly 400 can be decoupled from the tibial tuberosity 30 and the tibial body 23 and removed from the animal.

The advancement assembly 400 can be decoupled from the tibial tuberosity 30 and the tibial body 23 by removing the wires 466 and 497 from the tibial tuberosity 30 and the tibial body 23, respectively. Once decoupled, the advancement assembly 400 can be removed from the animal. A drill bit can be inserted through the fastener hole 118a to create a drill hole that is appropriate for the fastener 120. Then, the fastener 120 can be inserted through the fastener hole 118a and into the tibial tuberosity 30 to secure the implant 104 to the tibial tuberosity 30. Additional fasteners 120 can be inserted through the fasteners holes 118b, 118c, and 118d and into tibial tuberosity 30 as deemed necessary for a secure connection between the implant 104 and the tibial tuberosity 30.

Referring to FIGS. 3 and 10A-10I, in another embodiment, the TTA system 100 can include an alternate embodiment of the implant 104 (shown in FIG. 3), such as implant 604 (shown in FIGS. 10A-10H). The implant 604 can be constructed as a bone fixation member 606, such as a bone plate 608. In the depicted embodiment, the implant 604 includes an implant body 610 that includes a proximal end portion 612, an opposed distal end portion 614, and an intermediate implant portion 616 disposed between the proximal end portion 612 and the distal end portion 614. The proximal end portion 612 of the implant body 610 can be configured to be attached to the tuberosity 30 that has been advanced along with the patellar tendon 32 (shown in FIG. 1) in a direction cranially relative to the tibial body 23 from a first position to an advanced position. The distal end portion 614 of the implant body 610 can be configured to be attached to the tibial body 23.

It should be appreciated that the patellar tendon 32 is attached to the tuberosity 30 at an anatomical attachment location 43, and that the tuberosity 30 can be resected, and thus separated, from the tibial body 23 at a location caudal of the attachment location 43 such that the patellar tendon 32, including the attachment location 43, is advanced along with the separated tuberosity 30 from the first position to the advanced position. The proximal end portion 612, the distal end portion 614, and the intermediate implant portion 616 can collectively be a monolithic structure. Alternatively, proximal end portion 612, the distal end portion 614, and the intermediate implant portion 616 can be discrete components that are connected to each other to form the implant body 610.

The proximal end portion 612 can be contoured and configured to conform to a medial surface or lateral surface of the tuberosity 30 to facilitate attachment of the implant 604 to the tuberosity 30. Moreover, the proximal end portion 612 includes one or more attachment locations such as fastener holes. In the depicted embodiment, the proximal end portion 612 of the implant body 610 includes four fastener holes 618a, 618b, 618c, and 618d. However, the proximal end portion 612 may include more or fewer fastener holes. Each fastener hole 618a, 618b, 618c, and 618d extends through the implant body 610, and is configured and sized to receive a fastener 120, such as a bone anchor, that is capable of attaching the implant 604 to the tuberosity 30. The fastener holes 618a, 618b, 618c, and 618d can be threaded holes that are configured to receive a bone screw. In another embodiment the fasteners holes 618a, 618b, 618c, and 618d can be conical thread holes that are configured receive bone screws with a threaded or non-threaded conical head.

The insertion of fasteners 120 through fastener holes 618a, 618b, 618c, and 618d causes the proximal end portion 612 to be attached to the tuberosity 30. The fastener holes 618a, 618b, 618c, and 618d may be spaced apart from one another and substantially aligned along a first longitudinal axis L1' that extends substantially parallel to the direction of elongation of the tuberosity 30 when the implant 604 is attached to the advanced tuberosity 30. In one embodiment the proximal end portion 112 can be elongate along the longitudinal axis L1'.

The distal end portion 614 can be contoured and configured to conform to a medial surface or a lateral surface of the tibial body 23 to facilitate attachment of the implant 604 to the tibial body 23. Further, the distal end portion 614 of the implant body 610 can include one or more anchor locations such as fastener holes. In the illustrated embodiment, the distal end portion 614 includes fastener holes 622a, 622b, 622c, and 622d. Each of the fastener holes 622a, 622b, 622c, and 622d can be configured and sized to receive a fastener 124, such as a bone anchor, capable of attaching the implant 604 to the tibial body 23.

The insertion of fasteners 124 through the fastener holes 622a, 622b, 622c and 622d causes the distal end portion 614 to be attached to the tibial body 23. The fastener holes 622a, 622b, 622c, and 622d may be spaced apart from one another and substantially aligned along a second longitudinal axis L2'. In one embodiment the distal end portion 614 can be elongate along the second longitudinal axis L2'. The first longitudinal axis L1' may be angularly offset from the second longitudinal axis L2' such that an offset angle OA is defined. The first and second longitudinal axes L1' and L2' can be offset such that offset angle OA is between about 170 degrees and about 130 degrees. In another embodiment the first and second longitudinal axes L1' and L2' can be offset such that offset angle OA is about 150 degrees. In another embodiment the offset angle OA is about 180 degrees (or 0 degrees) such that the first and second longitudinal axes L1' and L2' are parallel or not angularly offset.

The intermediate implant portion 616 of the implant body 610 can be substantially curved. Alternatively, the intermediate implant portion 616 may be substantially straight and elongated along an axis that is either angularly offset from or parallel to the second longitudinal axis L2'. Although the drawings do not show attachment locations, such as fastener holes, in the intermediate implant portion 616, it is envisioned that the intermediate implant portion 616 may include one or more fastener holes or any other suitable attachment feature. The intermediate implant portion 616 extends between the proximal end portion 612 and the distal end portion 614 and is shaped so as to space the proximal end portion 612 cranially with respect to the distal end portion 614 an amount, or a distance, sufficient so as to maintain the tuberosity 30 in the advanced position.

The implant body 610 can further define a first surface 626 and a second surface 628 that is opposite the first surface 626. In one embodiment, the first surface 626 is configured to face a tibial body 23 and a tuberosity 30 of a tibia 22, and the second surface 628 is configured to face away from the tibial body 23 and the tuberosity 30, when the implant 604 is implanted adjacent to a tibia 22. In another embodiment, the second surface 628 is configured to face a tibial body 23 and a tuberosity 30 of a tibia 22, and the first surface 626 is configured to face away from the tibial body 23 and the tuberosity 30, when the implant 604 is implanted adjacent to a tibia 22.

The implant body 610 can define a thickness measured between the first surface 626 and the second surface 628. In one embodiment, the thickness of the plate can be constant along the implant body 610, for example as shown in FIG. 3. In another embodiment, the thickness of the implant body 610 can vary. For example the implant body 610 can define a proximal portion thickness T1, a distal portion thickness T2, and an intermediate portion thickness T3. As stated above, the proximal portion thickness T1, the distal portion thickness T2, and the intermediate portion thickness T3 can all be substantially equal. In another embodiment, the proximal portion thickness T1, the distal portion thickness T2, and the intermediate portion thickness T3 can be substantially unequal. For example, the intermediate implant portion 616 can include a thinned out or necked portion 630 that defines an intermediate portion thickness T3 that is less than at least one (or alternatively, both) of the proximal and distal portion thicknesses T1 and T2. The necked portion 630 and reduced intermediate portion thickness T3 can allow for the implant 604 to be bent or flexed such that first surface 626 corresponds more closely with the surfaces of the tibial body 23 and the tuberosity 30 then if the implant body 610 had a constant thickness. In another embodiment, each of the proximal portion thickness T1, the distal portion thickness T2, and the intermediate portion thickness T3, can be either greater than, less than, or equal to any of the other portion thicknesses.

In another embodiment the proximal end portion 612, the distal end portion 614, or both can include a thinned out or necked portion 630. The necked portion 630 of any of the proximal end portion 612, the distal end portion 614, or the intermediate portion 616 may only comprise a portion of the respective implant portion such that the respective thickness T1, T2, or T3 varies within that implant portion. The necked portion 630 can include at least one transition 632, for example two transitions 632, where the thickness of the implant body 610 changes. As shown in the illustrated embodiment, the transition 632 can be a radiused surface 633 resulting in a gradual change in thickness. In another embodiment the transition 632 can include a step resulting in a sudden change in thickness. In another embodiment, the transition 632 can include both a radiused surface 633 and a step surface resulting in a partial gradual change in thickness and a partial sudden change in thickness. In another embodiment the implant body 610 can include transitions 632 that are different, for example one transition 632 with a radiused surface 633 and another transition 632 with a step surface.

The implant body 610 can include a first side surface 634 and a second side surface 636 opposite the first side surface 634. The first and second side surfaces 634 and 636 can each extend between the first surface 626 and the second surface 628 in one direction, and between the proximal end portion 612 and the distal end portion 614 in another direction. The implant body 610 can define a width measured between the first side surface 634 and the second side surface 636. In one embodiment, the width of the plate can be constant along the implant body 610, for example as shown in FIG. 3. In another embodiment, the width of the implant body 610 can vary. For example the implant body 610 can define a proximal portion width W1, a distal portion width W2, and an intermediate portion width W3.

As stated above, the proximal portion width W1, the distal portion width W2, and the intermediate portion width W3 can all be substantially equal. In another embodiment, the proximal portion width W1, the distal portion width W2, and the intermediate portion width W3 can be substantially unequal. For example, the implant body 610 can include a neck 638 between the proximal end portion 612 and the intermediate implant portion 616, such that the width of the implant body 610 changes along the neck 638. As shown in the illustrated embodiment, the width of the implant body transitions along the neck 638 from the greater intermediate portion width W3 down to the smaller proximate portion width W1. In another embodiment, each of the proximal portion width W1, the distal portion width W2, and the intermediate portion width W3, can be either greater than, less than, or equal to any of the other portion widths.

In one embodiment the implant body 610 can include at least one scalloped portion 640. The scalloped portion 640 can include a peripheral side wall 642 and a raised surface 644. In one embodiment the raised surface 644 extends out from the first surface 626 and can be configured to face a tibial body 23 and a tuberosity 30 of a tibia 22 when the implant 604 is implanted adjacent to a tibia 22. In the illustrated embodiment, the distal end portion 614 includes scalloped portions 640a, 640b, 640c, and 640d. In one embodiment the scalloped portion 640 can include a partial peripheral side wall 642d that does not completely define the outer boundary of the scalloped portion 640d.

As shown in the illustrated embodiment, the implant body 610 can include adjacent scalloped portions 640, for example scalloped portions 640b and 640c or scalloped portions 640c and 640d. The adjacent scalloped portions 640 can be separated by a gap 646 that is defined by the facing portions of the peripheral side walls 642, for example 642b and 642c. The gap 646 can extend through an entirety of the width of the respective implant portion (proximal portion width W1, distal portion width W2, intermediate portion width W3) that carries the adjacent scalloped portions 640. In an alternative embodiment the gap 646 can extend only partially through the width of the respective implant portion that carries the adjacent scalloped portions 640. The gap 646 can vary in size along the width of the implant portion that carries the adjacent scalloped portions 640. For example, as shown in the illustrated embodiment, the gap 646 can be wider at the ends of the gap 646 along the width (adjacent the first and second side walls 634 and 636) and narrower around the middle of the gap 646 along the width.

The facing portions of the peripheral side walls 642b and 642c of the adjacent scalloped portions 640b and 640c can include a tapered portion, a substantially parallel portion, or both. In the substantially parallel portion the peripheral side walls 642b and 642c of the adjacent scalloped portions 640b and 640c extend along the width substantially parallel to each other such that the size of the gap 646 is substantially constant. In the tapered portion the peripheral side walls 642b and 642c of the adjacent scalloped portions 640b and 640c flare away from each other along the width. As shown in the illustrated embodiment, the peripheral side walls 642b and 642c of the adjacent scalloped portions 640b and 640c can flare away from each other linearly such that a first gap angle 648 is defined. The first gap angle 648 can be from about 45 degrees to about 135 degrees, or in another embodiment the first gap angle 648 can be about 90 degrees. In another embodiment the peripheral side walls 642b and 642c of the adjacent scalloped portions 640b and 640c can flare away from each other nonlinearly.

In addition to extending along the width of the plate, the gap 646 can extend along the thickness of the plate, for example the gap 646 can extend into the first surface 626 toward the second surface 628. In one embodiment the peripheral side walls 642b and 642c of the adjacent scalloped portions 640b and 640c flare away from each other along the thickness of the implant body 610. As shown in the illustrated embodiment, the peripheral side walls 642b and 642c of the adjacent scalloped portions 640b and 640c can flare away from each other linearly such that a second gap angle 650 is defined. The second gap angle 650 can be from about 0 degrees to about 60 degrees, or in another embodiment the second gap angle 650 can be about 30 degrees. In another embodiment the peripheral side walls 642b and 642c of the adjacent scalloped portions 640b and 640c can flare away from each other nonlinearly along the thickness.

Referring to FIGS. 3 and 11A-11I, in another embodiment, the TTA system 100 can include another embodiment of the implant 104 (shown in FIG. 3), such as implant 704 (shown in FIGS. 11A-11H). The implant 704 can be constructed as a bone fixation member 706, such as a bone plate 708. In the depicted embodiment, the implant 704 includes an implant body 710 that includes a proximal end portion 712, an opposed distal end portion 714, and an intermediate implant portion 716 disposed between the proximal end portion 712 and the distal end portion 714. The proximal end portion 712 of the implant body 710 can be configured to be attached to the tuberosity 30 that has been advanced along with the patellar tendon 32 (shown in FIG. 1) in a direction cranially relative to the tibial body 23 from a first position to an advanced position. The distal end portion 714 of the implant body 710 can be configured to be attached to the tibial body 23.

It should be appreciated that the patellar tendon 32 is attached to the tuberosity 30 at an anatomical attachment location 43, and that the tuberosity 30 can be resected, and thus separated, from the tibial body 23 at a location caudal of the attachment location 43 such that the patellar tendon 32, including the attachment location 43, is advanced along with the separated tuberosity 30 from the first position to the advanced position. The proximal end portion 712, the distal end portion 714, and the intermediate implant portion 716 can collectively be a monolithic structure. Alternatively, proximal end portion 712, the distal end portion 714, and the intermediate implant portion 716 can be discrete components that are connected to each other to form the implant body 710.

The proximal end portion 712 can be contoured and configured to conform to a medial surface or lateral surface of the tuberosity 30 to facilitate attachment of the implant 704 to the tuberosity 30. Moreover, the proximal end portion 712 includes one or more attachment locations such as fastener holes. In the depicted embodiment, the proximal end portion 712 of the implant body 710 includes four fastener holes 718a, 718b, 718c, and 718d. However, the proximal end portion 712 may include more or fewer fastener holes. Each fastener hole 718a, 718b, 718c, and 718d extends through the implant body 710, and is configured and sized to receive a fastener 120, such as a bone anchor, that is capable of attaching the implant 704 to the tuberosity 30. The fastener holes 718a, 718b, 718c, and 718d can be threaded holes that are configured to receive a bone screw. In another embodiment the fasteners holes 718a, 718b, 718c, and 718d can be conical thread holes that are configured receive bone screws with a threaded or non-threaded conical head.

The insertion of fasteners 120 through fastener holes 718a, 718b, 718c, and 718d causes the proximal end portion 712 to be attached to the tuberosity 30. The fastener holes 718a, 718b, 718c, and 718d may be spaced apart from one another and substantially aligned along a first longitudinal axis L1″ that extends substantially parallel to the direction of elongation of the tuberosity 30 when the implant 704 is attached to the advanced tuberosity 30. In one embodiment the proximal end portion 112 can be elongate along the longitudinal axis L1″.

The distal end portion 714 can be contoured and configured to conform to a medial surface or a lateral surface of the tibial body 23 to facilitate attachment of the implant 704 to the tibial body 23. Further, the distal end portion 714 of the implant body 710 can include one or more anchor locations such as fastener holes. In the illustrated embodiment, the distal end portion 714 includes fastener holes 722a, 722b, 722c, and 722d. Each of the fastener holes 722a, 722b, 722c, and 722d can be configured and sized to receive a fastener 124, such as a bone anchor, capable of attaching the implant 704 to the tibial body 23.

The insertion of fasteners 124 through the fastener holes 722a, 722b, 722c, and 722d causes the distal end portion 714 to be attached to the tibial body 23. The fastener holes 722a, 722b, 722c, and 722d may be spaced apart from one another and substantially aligned along a second longitudinal axis L2″. In one embodiment the distal end portion 714 can be elongate along the second longitudinal axis L2″. The first longitudinal axis L1″ may be angularly offset from the second longitudinal axis L2″ such that an offset angle OA′ is defined. The first and second longitudinal axes L1″ and L2″ can be offset such that offset angle OA′ is between about 180 degrees and about 160 degrees. In another embodiment the first and second longitudinal axes L1″ and L2″ can be offset such that offset angle OA′ is about 170 degrees. In another embodiment the offset angle OA′ is 180 degrees (or 0 degrees) such that the first and second longitudinal axes L1″ and L2″ are parallel or not angularly offset.

The intermediate implant portion 716 of the implant body 710 can be substantially curved. Alternatively, the intermediate implant portion 716 may be substantially straight and elongated along an axis that is either angularly offset from or parallel to the second longitudinal axis L2″. Although the drawings do not show attachment locations, such as fastener holes, in the intermediate implant portion 716, it is envisioned that the intermediate implant portion 716 may include one or more fastener holes or any other suitable attachment feature. The intermediate implant portion 716 extends between the proximal end portion 712 and the distal end portion 714 and is shaped so as to space the proximal end portion 712 cranially with respect to the distal end portion 714 an amount, or a distance, sufficient so as to maintain the tuberosity 30 in the advanced position.

The implant body 710 can further define a first surface 726 and a second surface 728 that is opposite the first surface 726. In one embodiment, the first surface 726 is configured to face a tibial body 23 and a tuberosity 30 of a tibia 22, and the second surface 728 is configured to face away from the tibial body 23 and the tuberosity 30, when the implant 704 is implanted adjacent to a tibia 22. In another embodiment, the second surface 728 is configured to face a tibial body 23 and a tuberosity 30 of a tibia 22, and the first surface 726 is configured to face away from the tibial body 23 and the tuberosity 30, when the implant 704 is implanted adjacent to a tibia 22.

The implant body 710 can define a thickness measured between the first surface 726 and the second surface 728. In one embodiment, the thickness of the plate can be constant along the implant body 710, for example as shown in FIG. 3. In another embodiment, the thickness of the implant body 710 can vary. For example the implant body 710 can define a proximal portion thickness T1′, a distal portion thickness T2′, and an intermediate portion thickness T3′. As stated above, the proximal portion thickness T1′, the distal portion thickness T2′, and the intermediate portion thickness T3′ can all be substantially equal. In another embodiment, the proximal portion thickness T1′, the distal portion thickness T2′, and the intermediate portion thickness T3′ can be substantially unequal. For example, the intermediate implant portion 716 can include a thinned out or necked portion 730 that defines an intermediate portion thickness T3′ that is less than at least one (or alternatively, both) of the proximal and distal portion thicknesses T1′ and T2′. The necked portion 730 and reduced intermediate portion thickness T3′ can allow for the implant 704 to be bent or flexed such that first surface 726 corresponds more closely with the surfaces of the tibial body 23 and the tuberosity 30 then if the implant body 710 had a constant thickness. In another embodiment, each of the proximal portion thickness T1′, the distal portion thickness T2′, and the intermediate portion thickness T3′, can be either greater than, less than, or equal to any of the other portion thicknesses.

In another embodiment the proximal end portion 712, the distal end portion 714, or both can include a thinned out or necked portion 730. The necked portion 730 of any of the proximal end portion 712, the distal end portion 714, or the intermediate portion 716 may only comprise a portion of the respective implant portion such that the respective thickness T1′, T2′, or T3′ varies within that implant portion. The necked portion 730 can include at least one transition 732, for example two transitions 732, where the thickness of the implant body 710 changes. As shown in the illustrated embodiment, the transition 732 can be a radiused surface 733 resulting in a gradual change in thickness. In another embodiment the transition 732 can include a step resulting in a sudden change in thickness. In another embodiment, the transition 732 can include both a radiused surface 733 and a step surface resulting in a partial gradual change in thickness and a partial sudden change in thickness. In another embodiment the implant body 710 can include transitions 732 that are different, for example one transition 732 with a radiused surface 733 and another transition 732 with a step surface.

The implant body 710 can include a first side surface 734 and a second side surface 736 opposite the first side surface 734. The first and second side surfaces 734 and 736 can each extend between the first surface 726 and the second surface 728 in one direction, and between the proximal end portion 712 and the distal end portion 714 in another direction. The implant body 710 can define a width measured between the first side surface 734 and the second side surface 736. In one embodiment, the width of the plate can be constant along the implant body 710, for example as shown in FIG. 3. In another embodiment, the width of the implant body 710 can vary. For example the implant body 710 can define a proximal portion width W1', a distal portion width W2', and an intermediate portion width W3'.

As stated above, the proximal portion width W1', the distal portion width W2', and the intermediate portion width W3' can all be substantially equal. In another embodiment, the proximal portion width W1', the distal portion width W2', and the intermediate portion width W3' can be substantially unequal. For example, the implant body 710 can include a neck 738 between the proximal end portion 712 and the intermediate implant portion 716, such that the width of the implant body 710 changes along the neck 738. As shown in the illustrated embodiment, the width of the implant body transitions along the neck 738 from the greater intermediate portion width W3' down to the smaller proximate portion width W1'. In another embodiment, each of the proximal portion width W1', the distal portion width W2', and the intermediate portion width W3', can be either greater than, less than, or equal to any of the other portion widths.

In one embodiment the implant body 710 can include at least one scalloped portion 740. The scalloped portion 740 can include a peripheral side wall 742 and a raised surface 744. In one embodiment the raised surface 744 extends out from the first surface 726 and can be configured to face a tibial body 23 and a tuberosity 30 of a tibia 22 when the implant 704 is implanted adjacent to a tibia 22. In the illustrated embodiment, the distal end portion 714 includes scalloped portions 740a, 740b, 740c, and 740d. In one embodiment the scalloped portion 740 can include a partial peripheral side wall 742d that does not completely define the outer boundary of the scalloped portion 740d.

As shown in the illustrated embodiment, the implant body 710 can include adjacent scalloped portions 740, for example scalloped portions 740b and 740c or scalloped portions 740c and 740d. The adjacent scalloped portions 740 can be separated by a gap 746 that is defined by the facing portions of the peripheral side walls 742, for example 742b and 742c. The gap 746 can extend through an entirety of the width of the respective implant portion (proximal portion width W1', distal portion width W2', intermediate portion width W3') that carries the adjacent scalloped portions 740. In an alternative embodiment the gap 746 can extend only partially through the width of the respective implant portion that carries the adjacent scalloped portions 740. The gap 746 can vary in size along the width of the implant portion that carries the adjacent scalloped portions 740. For example, as shown in the illustrated embodiment, the gap 746 can be wider at the ends of the gap 746 along the width (adjacent the first and second side walls 734 and 736) and narrower around the middle of the gap 746 along the width.

The facing portions of the peripheral side walls 742b and 742c of the adjacent scalloped portions 740b and 740c can include a tapered portion, a substantially parallel portion, or both. In the substantially parallel portion the peripheral side walls 742b and 742c of the adjacent scalloped portions 740b and 740c extend along the width substantially parallel to each other such that the size of the gap 746 is substantially constant. In the tapered portion the peripheral side walls 742b and 742c of the adjacent scalloped portions 740b and 740c flare away from each other along the width. As shown in the illustrated embodiment, the peripheral side walls 742b and 742c of the adjacent scalloped portions 740b and 740c can flare away from each other linearly such that a first gap angle 748 is defined. The first gap angle 748 can be from about 45 degrees to about 135 degrees, or in another embodiment the first gap angle 748 can be about 90 degrees. In another embodiment the peripheral side walls 742b and 742c of the adjacent scalloped portions 740b and 740c can flare away from each other nonlinearly.

In addition to extending along the width of the plate, the gap 746 can extend along the thickness of the plate, for example the gap 746 can extend into the first surface 726 toward the second surface 728. In one embodiment the peripheral side walls 742b and 742c of the adjacent scalloped portions 740b and 740c flare away from each other along the thickness of the implant body 710. As shown in the illustrated embodiment, the peripheral side walls 742b and 742c of the adjacent scalloped portions 740b and 740c can flare away from each other linearly such that a second gap angle 750 is defined. The second gap angle 750 can be from about 0 degrees to about 45 degrees, or in another embodiment the second gap angle 750 can be about 10 degrees. In another embodiment the peripheral side walls 742b and 742c of the adjacent scalloped portions 740b and 740c can flare away from each other nonlinearly along the thickness.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A tibial tuberosity advancement system configured to maintain a tuberosity that has been moved cranially from an initial position to an advanced position, in the advanced position, the tibial tuberosity advancement system comprising:

an implant including an implant body, the implant body defining a proximal end portion, a distal end portion, and an intermediate portion that extends between the proximal end portion and distal end portion, the intermediate portion shaped such that when the distal end portion is attached to the tibial body a first surface of the proximal end portion faces the tuberosity, and a second surface of the proximal end portion is opposite the first surface along a first direction, the implant body including:

at least one fastener hole that extends through the proximal end portion from the first surface to the second surface along a central axis that extends along a second direction, the first surface defining a first opening of the fastener hole, the first opening including a first point and a second point diametrically opposed to the first point, the second surface defining a second opening of the fastener hole, the second opening including a third point and a fourth point diametrically opposed to the third point, the third point aligned with the first point along the second direction, and the fourth point aligned with the second point along the second direction;

a first side surface of the proximal end portion; and a second side surface of the proximal end portion that is opposite the first side surface with respect to a third direction that is perpendicular to the first direction, wherein the first point is between the first side surface and the second point with respect to the third direction, wherein the implant body is configured such that a first straight line: 1) passes through each of the first side surface, the first point, the second point, and the second side surface; 2) defines a first distance measured along the first straight line from the first point to the first side surface; and 3) defines a second distance measured along the first straight line from the second point to the second side surface, the first distance being less than the second distance, and wherein the implant body is configured such that a second straight line: 1) passes through each of the first side surface, the third point, the fourth point, and the second side surface; 2) defines a third distance measured along the second straight line from the third point to the first side surface; and 3) defines a fourth distance measured along the second straight line from the fourth point to the second side surface, the third distance being greater than the fourth distance;

a spacer configured and sized to fit at least partially within a gap disposed between the tuberosity and the tibial body when the tuberosity is in the advanced position; and a spacer fixation member that includes a first end portion configured to be attached to the tuberosity, a second end portion that is configured to be attached to the tibial body, and an intermediate fixation portion that extends between the first end portion and the second end portion, the intermediate fixation portion configured to be coupled to the spacer.

2. The tibial tuberosity advancement system of claim according to claim 1, wherein both the first central axis and the second central axis are nonparallel with respect to the direction.

3. The tibial tuberosity advancement system of claim according to claim 1, wherein the spacer includes a spacer body, the spacer defines a slot that extends through the spacer body, and the intermediate fixation portion is configured and sized to be at least partially received in the slot so as to couple the spacer fixation member to the spacer.

4. The tibial tuberosity advancement system according to claim 1, wherein the spacer includes a plurality of resilient tines, each of the resilient tines configured to be moved toward one another when the spacer is disposed in the gap such that at least a portion of the spacer conforms to a shape of the gap.

5. The tibial tuberosity advancement system according to claim 4, wherein the spacer defines at least one first fastener hole that is configured to receive a fastener, the at least one fastener hole extends into the spacer body, the intermediate fixation portion defines at least one second fastener hole, and the fastener is configured to be inserted through the at least one second fastener hole and into the at least one first fastener hole to couple the spacer fixation member to the spacer.

6. The tibial tuberosity advancement system according to claim 4, wherein the spacer body defines an upper surface and an opposed lower surface, and the lower surface defines a substantially concave shape to facilitate movement of the resilient tines toward each other when the spacer is disposed in the gap.

7. The tibial tuberosity advancement system according to claim 1, wherein the at least one fastener hole comprises a plurality of fastener holes, and the tibial tuberosity advancement system further comprises a plurality of fasteners configured to be separately individually inserted into a respective one of the plurality of fastener holes so as to secure the proximal end portion to the tuberosity.

8. The tibial tuberosity advancement system according to claim 7, wherein the plurality of fastener holes is a first plurality of fastener holes, and the distal end portion defines a second plurality of fastener holes each configured to receive a fastener so as to attach the distal end portion to the tibial body, wherein the second plurality of fastener holes extend through the distal end portion along respective central axes that are oriented along the first direction.

* * * * *